United States Patent [19]

Aburatani et al.

[11] Patent Number: 4,861,875
[45] Date of Patent: Aug. 29, 1989

[54] 3α,5-CYCLO-22,23-DIHYDROXY-5α-STEROID COMPOUNDS

[75] Inventors: Masakazu Aburatani, Takaoka; Tadashi Takeuchi, Himi; Kenji Mori, Tokyo, all of Japan

[73] Assignees: Fuji Yakuhin Kogyo Kabushiki Kaisha; National Federation of Agricultural Co-Operative Associations, Tokyo, Japan

[21] Appl. No.: 858,129

[22] Filed: May 1, 1986

[30] Foreign Application Priority Data

May 1, 1985 [JP] Japan .................................. 60-92199

[51] Int. Cl.$^4$ ............................................. C07J 17/00
[52] U.S. Cl. .................................. 540/114; 260/397.1; 260/397.3; 260/397.4; 260/397.5
[58] Field of Search ............... 260/397.1, 397.3, 397.4, 260/397.5; 549/454; 540/114

[56] References Cited

U.S. PATENT DOCUMENTS 3,337,591  8/1967  Freiberg et al. ................. 260/397.1
4,545,938  10/1985  Mosbach et al. ................. 260/397.1

OTHER PUBLICATIONS

Kozikowski et al., J.A.C.S., 1980, vol. 102, pp. 6580–6581.
Chemical Abstracts, vol. 92, No. 7, Abstract 59104q, p. 708, Feb. 18, 1980.
Chemical Abstracts, vol. 97, No. 5, Abstract 36080t, p. 312, Aug. 2, 1982.
Chemical Abstracts, vol. 106, No. 13, Abstract 102,614c, p. 692, Mar. 30, 1987.

Primary Examiner—Mary C. Lee
Assistant Examiner—Zinna Northington
Attorney, Agent, or Firm—Birch, Stewart, Kolasch & Birch

[57] ABSTRACT

New steroid compounds of the general formula:

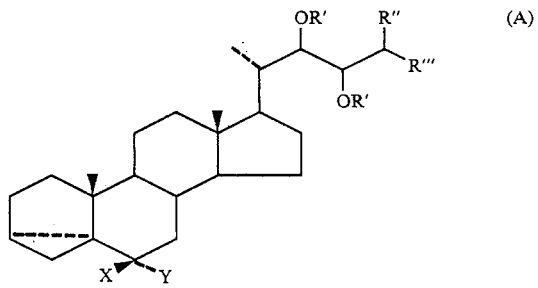

wherein X is a hydroxyl group and Y is a hydrogen atom, or X and Y, taken together, form an oxo group; each of the two R' radicals is independently a hydrogen atom, acyl group, a silyl group, an alkoxycarbonyl group or a benzyl group, or the two R' radicals, taken together, form an alkylidene or a carbonyl group, the stereo-configuration at the 22- and 23-positions being either 22R and 23R or 22S and 23S; and R" and R''' are independently of each other a hydrogen atom or a lower alkyl group, as well as processes for preparing same. These new steroid compounds are valuable intermediates for brassinolide and its analogues useful as plant hormones.

12 Claims, No Drawings

3α,5-CYCLO-22,23-DIHYDROXY-5α-STEROID COMPOUNDS

BACKGROUND OF THE INVENTION

1. Field of the Invention

The present invention relates new steroid compounds as important intermediates for the synthesis of brassinosteroids as well as a process for preparing same. More particularly, the present invention relates to new 3α,5-cyclo-22,23-dihydroxy-5α-steroid compounds of the general formula:

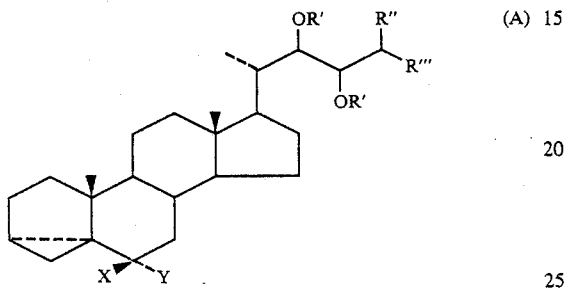

wherein X is a hydroxyl group and Y is a hydrogen atom, or X and Y, taken together, form an oxo group; each of the two R' radicals is independently a hydrogen atom, an acyl group, a silyl group, an alkoxycarbonyl group or a benzyl group, or the two R' radicals, taken together, form an alkylidene or a carbonyl group, the stereo-configuration at the 22- and 23-positions being either 22R and 23R or 22S and 23S; and R" and R''' are independently of each other a hydrogen atom or a lower alkyl group, as well as a process for preparing same.

2. Description of the Prior Art

Brassinolide is a steroidal compound with a plant-growth regulating activity isolated in 1979 from pollens of *Brassica napus* L. and structurally determined to be (2R,3S,22R,23R,24S)-2,3,22,23-tetrahydroxy-24-methyl-B-homo-7-oxa-5α-cholestan-6-one [Nature 281, 216–217 (1979)]. Brassinolide is considered to be the 6th plant hormone subsequent to ethylene, auxin, gibberellin, cytokinin and abscicic acid, and is still being studied for its distribution in plants and its specific functions thereto. Thus, a number of processes have been reported hitherto for the synthesis of brassinolide and its analogues (generally called brassinosteroids) as well as their intermediate products, including J. B. Siddall et al., J. Am. Chem. Soc., 102, 6580, (1980); N. Ikekawa et al., J. Chem. Soc. Chem. Comn., 1980, 962 and J. Chem. Soc. Perkin Trans. I, 1984, 139; H. Nozaki et al., J. Am. Chem. Soc., 105, 4491, (1983); T. C. McMorris et al., J. Org. Chem., 49, 2833, (1984); J. Tsuji et al., Tetrahedron Letters, 26, 69, (1985); A. Ficchi et al., J. Org. Chem., 49, 4297, (1984); N. B. Mandana et al., Steroids, 38, 2864, (1981); K. Mori et al., Tetrahedron, 38, 2099, (1982); A. Ficchi et al., J. Chem. Soc. Perkin Trans. I, 1983, 383; and K. Mori et al., Tetrahedron, 40, 1767, (1984). As the structure of brassinosteroids is complicate, the synthesis of brassinosteroids requires a sequence of chemical reactions and usually consists of more than ten steps. The majority of the reported synthetic processes for brassinosteroids, e.g. the former seven processes are now carried out through the route as shown in the following Scheme 1 (the process of Siddall et al.):

Scheme 1

Process of Siddall et al. [J. Am. Chem. Soc. 102 6580 (1980)]

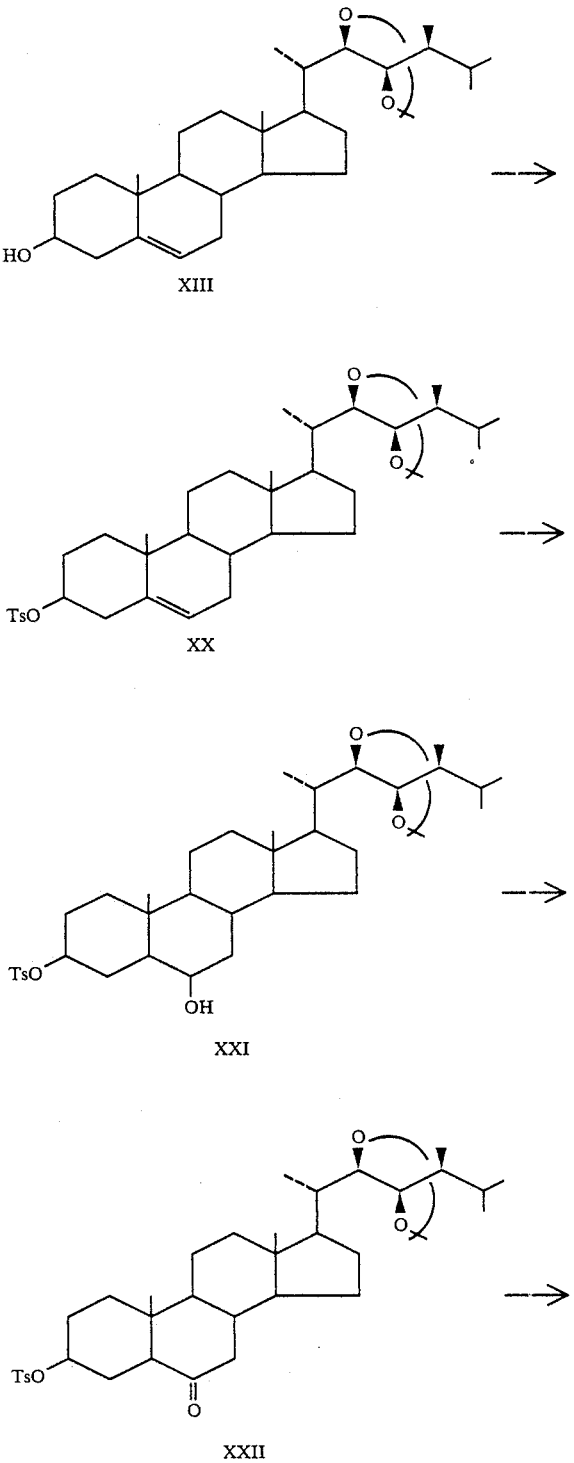

-continued
Scheme 1
Process of Siddall et al. [J. Am. Chem. Soc. 102 6580 (1980)]

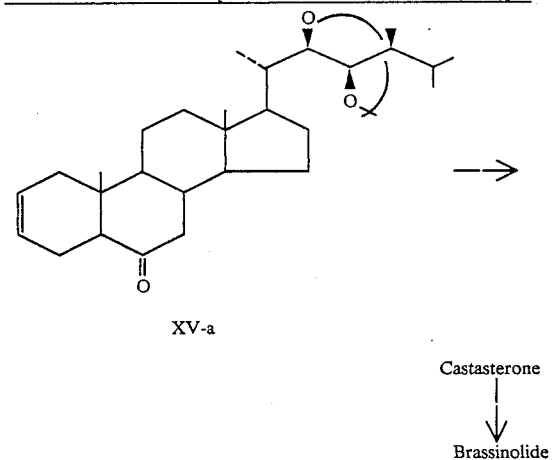

XV-a

Castasterone
↓
Brassinolide

Remarks: TsO represents p-toluenesulfonyloxy.

——→ Prior art process

According to the Siddall et al. process shown in Scheme 1, a known 3-hydroxy-5$^\Delta$-compound of the formula XIII is first converted with p-toluenesulfonyl chloride in pyridine into the corresponding 3-tosyloxy-5$^\Delta$-compound of the formula XX wherein the hydroxyl group in 3-position is protected by the ester group, and the latter 3-protected compound is then reacted with BH$_3$ in tetrahydrofuran and H$_2$O$_2$ in an aqueous solution of sodium hydroxide to form the corresponding 3-tosyloxy-6β-hydroxy compound of the formula XXI. Next, the compound of the formula XXI is oxidized with pyridinium hydrochloride-chromic anhydride in methylene chloride to form the corresponding 3-tosyloxy-6-oxo compound of the formula XXII which is then reacted with LiBr in dimethylformamide to form a 2$^\Delta$-6-oxo compound of the formula XV-a which is one of the important known intermediate for the synthesis of brassinolide and its analogues.

The starting 3-hydroxy-5$^\Delta$-compound of the formula XIII can be prepared via several steps from stigmasterol according to one of the known processes as mentioned above. On the other hand, synthesis of brassinolide from the compound of the formula XV-a is known from several reports, for example, Ikekawa et al., J. Chem. Soc. Perkin Trans. I, 1984, 139. According to the Ikekawa et al. process, the compound of the formula XV-a is reacted with osmium tetraoxide and N-methylmorpholine oxide in n-butanol, tetrahydrofuran and water to form the corresponding 2α,3α-dihydroxy compound which is then treated with an aqueous solution of acetic acid to split off the acetonide group bonded to 22- and 23-positions thereby producing castasterone (2α,-3α,22β,23β-tetrahydroxy-6-one compound). For acylation of the hydroxyl groups, castasterone is reacted with acetic anhydride and DMAP in the presence of pyridine to form the corresponding 2α,3α,22β,23β-tetraacetoxy-6-one compound which is then converted to brassinolide by introducing 7-oxa group into the ring B.

The process of Siddall et al. comprised of 4 steps for preparing the compound of the formula XV-a from the compound of the formula XIII involves in the step for preparing the compound XXI from the compound of the formula XX the use of diborane which is expensive and cumbersome to handle. Thus, the process of Siddall et al. is not suitable as a synthetic process for brassinolide on an industrial scale.

Further, a number of processes are proposed for the synthesis of brassinolide from stigmasterol not via the route wherein the compound of the formula XV-a. Among the known references aforementioned, for example, the latter four references disclose the routes for the synthesis of brassinolide not via the compound of the formula XV-a. However, these known processes involve a number of steps and afford brassinolide in a very low yield. Up to the present, the process of Mori et al. comprised of 16 steps in all is regarded to be the best process and affords brassinolide in the maximum total yield as high as 3%. Thus, there is a necessity in the synthesis of brassinolide and its analogues to make further improvement in these known processes for reducing the number of the steps thereby increasing the total yield of brassinolide. For this purpose, it is necessary to find a new route for reducing the number of the steps over the whole or part of the process for synthesizing brassinolide from stigmasterol.

Starting from stigmasterol, a number of processes, including the process of Siddall et al., are known for the synthesis of the compound of the formula XIII which is an intermediate for the synthesis of brassinolide through a route wherein the compound of the formula XV-a is prepared. However, these known processes involve steps wherein the reaction is complicate or difficult and the yield of the product is poor, and are not satisfactory for a process to be carried out on an industrial scale.

For the synthesis of brassinosteroids in a more economical manner and in a smaller number of steps, there is a great demand in the field of this art for improving the steps hardly operable on an industrial scale in the prior art processes or developing a new route for synthesizing brassinosteroids which can be carried out economically and industrially.

BRIEF SUMMARY OF THE INVENTION

Accordingly, it is an object of the present invention to provide new steroidal compounds useful as intermediates for the synthesis of brassinosteroids.

It is another object of the present invention to provide a new process for preparing intermediates for the synthesis of brassinosteroids.

It is still another object of the present invention to provide a new advantageous route for preparing intermediates for the synthesis of brassinosteroids.

It is further object of the present invention to render the number of the steps in a process for synthesizing brassinosteroids smaller so that the process may be carried out economically.

It is still further object of the present invention to make an improvement in the steps involving chemical and economical difficulties in the process for synthesizing brassinosteroids so that the steps may be carried out smoothly on an industrial scale.

Other and further objects, features and advantages of the present invention will become apparent more fully from the following description.

DETAILED DESCRIPTION OF THE INVENTION

To fill the great demand in this art, the present inventors have made extensive researches for overcoming disadvantages in some steps in the prior art processes for synthesizing brassinosteroids and for developing a new economical route for preparing intermediate products for the synthesis of brassinolisteroids, which can be substituted for the relevant steps in the prior art processes wherein the reactions are complicate or require expensive reagents so that the preparation of the steroidal compounds is difficult to work on an industrial scale. As a result of the extensive researches for developing an industrially advantageous process for synthesizing brassinosteroids, it has now been found that the prior art process for preparing the compound of the formula XV-a from the compound of the formula XIII via the compound of the formula XXI according to Siddall et al. which involves a step unsuited for being carried out industrially can be replaced with a new process passing through a new route involving industrially advantageous steps. Further, it has also been found that the prior art process for preparing the compound of the formula XIII from stigmasterol can be substituted by a new efficient process passing through a different route involving specific short-circuit steps and that new intermediate steroidal compounds can be prepared from a certain known compound obtained on the way of synthesizing brassinosteroids according to the prior art process and a new industrially advantageous route for synthesizing brassinolide can be established from the new intermediate steroidal compounds. The present invention has been accomplished on the basis of the above finding.

According to one embodiment of the present invention, there is provided new 3α,5-cyclo-22,23-di(OR')-5α-steroid compounds of the general formula:

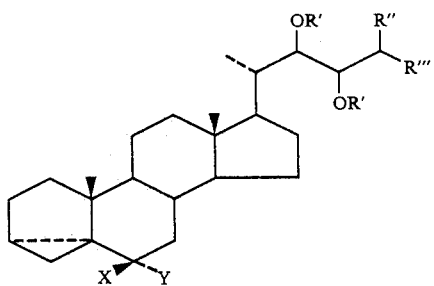

wherein X is a hydroxyl group and Y is a hydrogen atom, or X and Y, taken together, form an oxo group; each of the two R' radicals is independently a hydrogen atom, an acyl group, a silyl group, an alkoxycarbonyl group or a benzyl group, or the two R' radicals, taken together, form an alkylidene or a carbonyl group, the stereo-configuration at the 22- and 23-positions being either 22R and 23R or 22S and 23S; and R" and R''' are independently of each other a hydrogen atom or a lower alkyl group.

In one aspect of this embodiment, the compounds of the general formula (A) include 3α,5-cyclo-6-one compounds of the general formula (B):

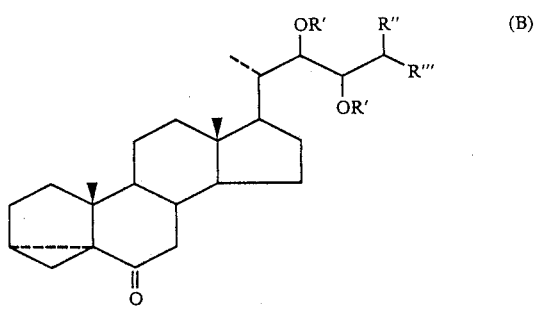

wherein each R' is a hydrogen atom, an acyl group, a silyl group, an alkoxycarbonyl group or a benzyl group, or the two R' radicals, taken together, form an alkylidene group or a carbonyl group, the stereo-configuration at the 22- and 23-positions being either 22R and 23R or 22S and 23S; and R" and R''' are independently of each other a hydrogen atom or a lower alkyl group.

In another aspect of this embodiment, the compounds of the general formula (A) include 3α,5-cyclo-6β-ol compounds of the general formula (C):

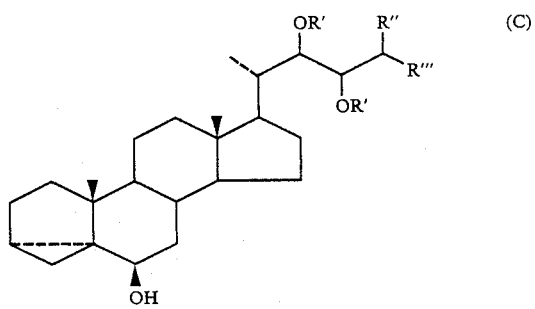

wherein each R' is a hydrogen atom, an acyl group, a silyl group, an alkoxycarbonyl group or a benzyl group, or the two R' radicals, taken together, form an alkylidene group or a carbonyl group, the stereo-configuration at the 22- and 23-positions being either 22R and 23R or 22S and 23S; and R" and R''' are independently of each other a hydrogen atom or a lower alkyl group.

In these formulas, R' in case of an acyl group is preferably a residue of a lower ($C_1-C_4$) alkanoic acid, e.g. acetyl, propionyl or butyryl, with acetyl being most preferable. Examples of R' in case of an alkoxycarbonyl group include one having 1–4 carbon atoms in the alkoxy moiety, such as methoxycarbonyl, ethoxycarbonyl, propoxycarbonyl or butoxycarbonyl. Preferable examples of the alkylidene group formed by the two R' radicals include isopropylidene, n-butylidene-2 and pentylidene-3, with the isobutylidene derived from acetone being most preferable. The radicals R" and R''' in case of a lower alkyl group have 1–4 carbon atoms and are preferably methyl or ethyl.

Illustrative of the 3α,5-cyclo-6-one compounds of the formula (B) are, for example, (22R,23R,24S)-3α,5-cyclo-22,23-diisopropylidenedioxy-24-methyl-5α-cholestan-6-one of the following formula I-a, (22R,23R,24S)-3α,5-cyclo-22,23-diacetoxy-24-methyl-5α-cholestan-6-one of the following formula I-c, (22S,23S,24S)-3α,5-cyclo-22,23-dihydroxy-24-methyl-5α-cholestan-6-one of the following formula I-d, (22S,23S,24S)-3α,5-cyclo-22,23-isopropylidenedioxy-24-methyl-5α-cholestan-6-one of the general formula I-e, (22S,23S,24S)-3α,5-cyclo-22,23-diacetoxy-24-ethyl-5α-cholestan-6-one of the following formula I-f and (22R,23R,24S)-3α,5-cyclo-22,23-diacetoxy-5α-cholestan-6-one of the following formula I-g:

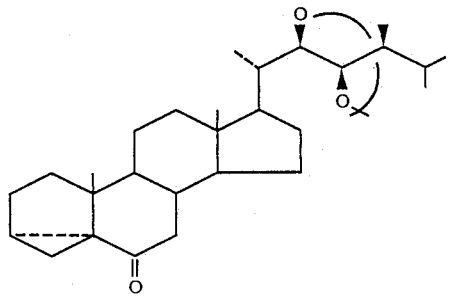
(I-a)

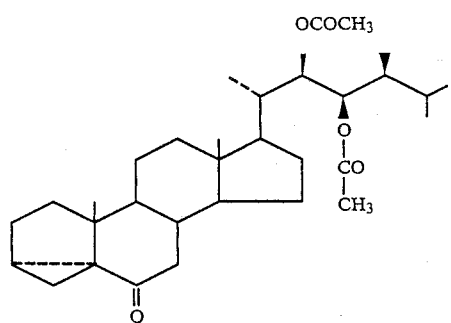
(I-c)

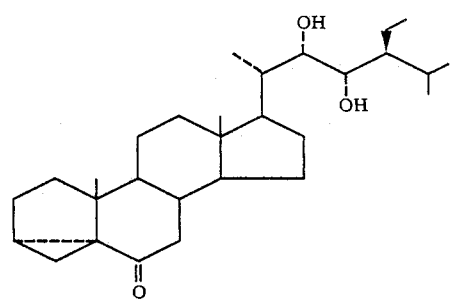
(I-d)

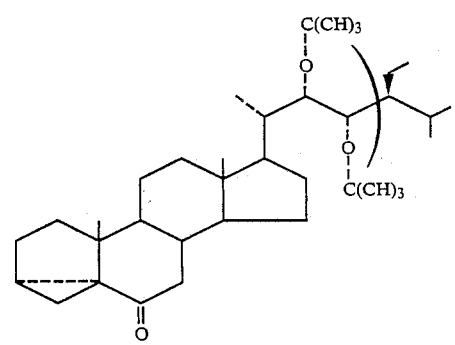
(I-e)

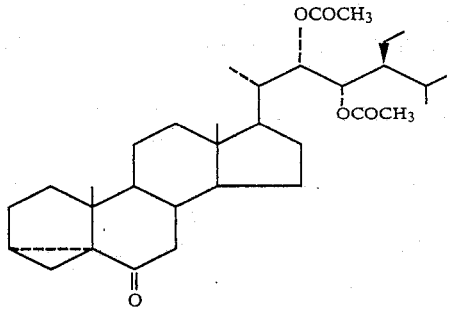
(I-f)

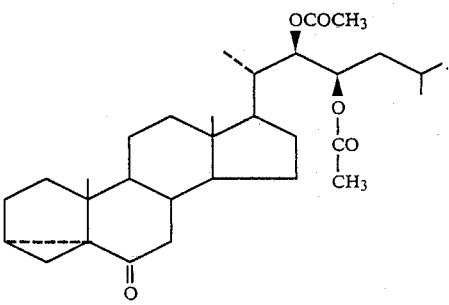
(I-g)

Illustrative of the 3α,5-cyclo-6β-ol compounds of the formula (C) are, for example, (22R,23R,24S)-3α,5-cyclo-22,23-isopropylidenedioxy-24-methyl-5α-cholestan-6β-ol of the following formula II-a, (22R,23R,24S)-3α,5-cyclo-22,23-dihydroxy-24-methyl-5α-cholestan-6β-ol of the following formula II-b, (22R,23R,24S)-3α,5-cyclo-22,23-diacetoxy-24-methyl-5α-cholestan-6β-ol of the following formula II-c and (22R,23R)-3α,5-cyclo-22,23-diacetoxy-5α-cholestan-6β-ol of the following formula II-g:

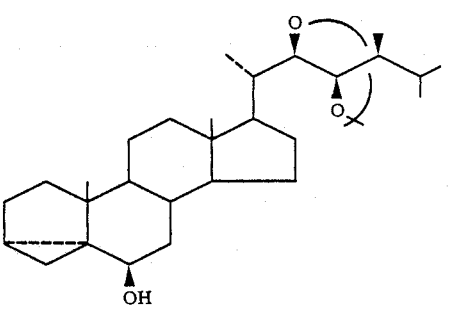
(II-a)

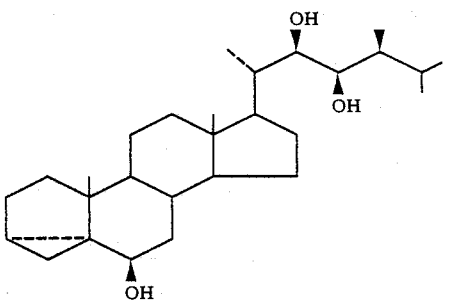
(II-b)

-continued

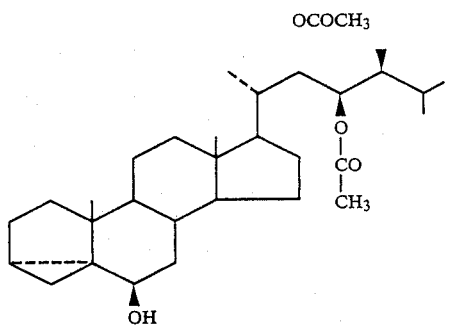
(II-c)

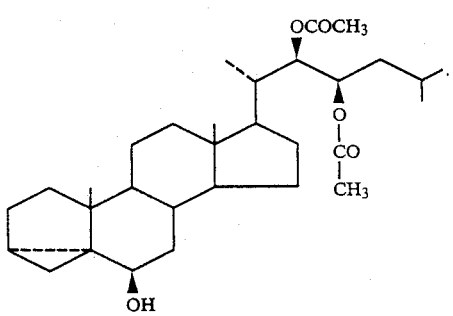
(II-g)

According to another embodiment of the present invention, there are provided new processes for preparing the new 3α,5-cyclo-22,23-di(OR')-5α-steroid compounds of the general formula (A).

In one aspect of this embodiment, there is provided a process for the preparation of a 3α,5-cyclo-22,23-alkylidenedioxy-5α-steroid compound of the general formula:

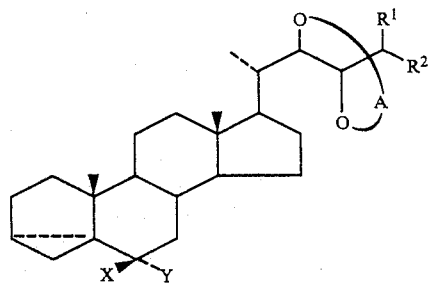
(D)

wherein X is a hydroxyl group and Y is a hydrogen atom, or X and Y, taken together, form an oxo group; A is an alkylidene group, the stereo-configuration at the 22- and 23-positions being either 22R and 23R or 22S and 23S; and $R^1$ and $R^2$ are independently of each other a lower alkyl group, which comprises reacting a 22,23-alkylidenedioxy-cholest-5-en-3β-ol of the general formula:

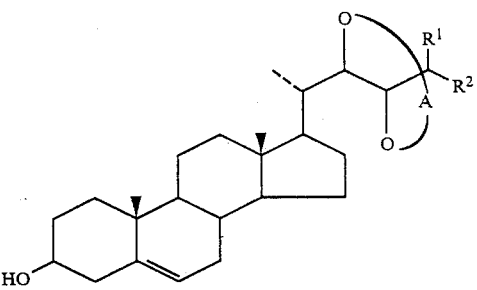
(E)

wherein A, $R^1$ and $R^2$ have the same meanings as given above and the stereo-configuration at the 22- and 23-positions is either 22R and 23R or 22S and 23S, with an acylating agent in the presence of an acid-binding agent to form the corresponding 3-acyloxy-5Δ-compound and thereafter treating the 3-acyloxy-5Δ-compound with an alkali metal carbonate or bicarbonate to form the corresponding 3α,5-cyclo-22,23-alkylidenedioxy-5α-cholestan-6β-ol compound, and optionally reacting the 6β-ol compound with an oxidizing agent.

In another aspect of this embodiment, there is provided a process for the preparation of a 3α,5-cyclo-22,23-substituted dihydroxy-5α-steroid compound of the general formula:

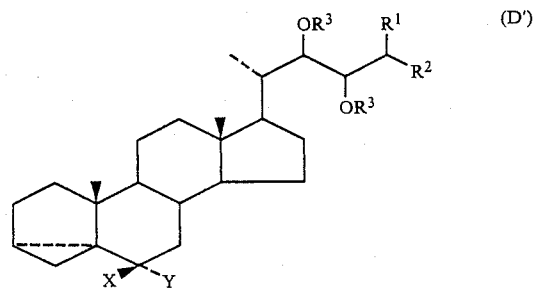
(D')

wherein X is a hydroxyl group and Y is a hydrogen atom, or X and Y, taken together, form an oxo group, $R^1$ and $R^2$ are independently of each other a lower alkyl group; and $R^3$ is an acyl group, a silyl group, an alkoxycarbonyl group or a benzyl group, or the two $R^3$ radicals, taken together, form an alkylidene group or a carbonyl group, the stereo-configuration at the 22- and 23-positions being either 22R and 23R or 22S and 23S, which comprises treating stigmasterol, after mesylation at the 3-position with a mesyl halide and an acid-binding agent to protect the 3β-hydroxyl group, with benzyl alcohol, a polar solvent and a weak base to form 24S-ethyl-3α,5-cyclo-6β-benzyloxy-5α-cholest-22-ene, reacting it with ozone in the presence of a weak base and then with a dialkyl sulfide to form 3α,5-cyclo-6β-benzyloxy-20S-formyl-5α-pregnane, reacting the pregnane with lithium isobutyne-1 under super-cooling to form 3α,5-cyclo-6β-benzyloxy-22R-hydroxy-5α-cholest-23-yne, catalytically hydrogenating the cholest-23-yne in the presence of P2-nickel catalyst to form the corresponding cholest-23-ene compound, reacting the latter with a peroxide to form (22R,23S,24R)-3α,5-cyclo-6β-benzyloxy-22-hydroxy-23,24-epoxy-5α-cholestan, reacting the epoxy compound with trimethyl aluminum and n-butyl lithium under super-cooling to form (22R,23R,24S)-3α,5-cyclo-6β-benzyloxy-22,23-dihydroxy-24-methyl-5α-cholestane, reacting the cholestane with an agent capable of introducing OR³ groups into the 22- and 23-positions to form the corresponding 22,23-di(OR³)-6β-benzyloxy compound, and thereafter subjecting the latter to hydrogenolysis to split off the benzyl group in the 6β-position, and optionally reacting the resultant 6β-ol compound with an oxidizing agent.

In still another aspect of this embodiment, there is provided a process for the preparation of a 3α,5-cyclo-22,23-substituted dihydroxyl-5α-steroid compound of the general formula:

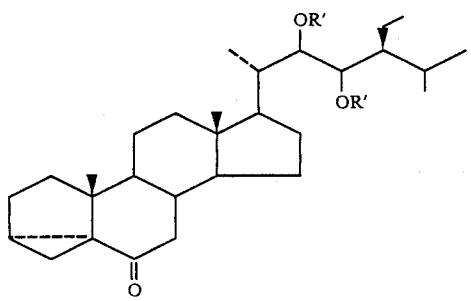

(B')

wherein R' is a hydrogen atom, an acryl group, a silyl group, an alkoxycarbonyl group or a benzyl group, or the two R' radicals, taken together, form an alkylidene group or a carbonyl group, the stereo-configuration at the 22- and 23-positions being either 22R and 23R or 22S and 23S, which comprises reacting 3α,5-cyclo-24S-ethyl-5α-cholest-22-en-6-one with osmium tetraoxide and N-methylmorpholine oxide to form (22S,23S,24S)-3α,5-cyclo-22,23-dihydroxy-24-methy-5α-cholestan-6-one and optionally treating this 22,23-dihydroxy compound with a reagent capable of converting the 22,23-dihydroxyl groups to OR' groups other than the hydroxyl groups.

In further aspect of this embodiment, there is provided a process for the preparation of a 3α,5-cyclo-22,23-substituted dihydroxyl-5α-steroid compound of the general formula:

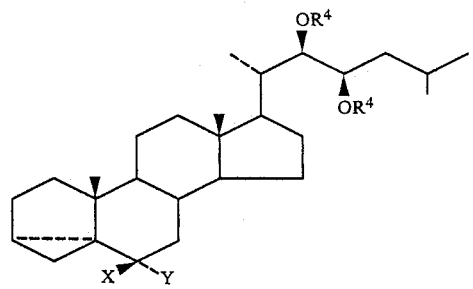

(D")

wherein X is a hydroxyl group and Y is a hydrogen atom or X and Y, taken together, form an oxo group, each R⁴ is an acyl group, a silyl group, an alkoxycarbonyl group or a benzyl group, the stereo-configuration at the 22- and 23-positions being either 22R and 23R, or 22S and 23S, which comprises treating stigmasterol, after mesylation at the 3-position with a mesyl halide and an acid-binding agent to protect the 3β-hydroxyl group, with benzyl alcohol, a polar solvent and a weak base to form 24S-ethyl3α,5-cyclo-6β-benzyloxy-5α-cholest-22-ene, reacting it with ozone in the presence of a weak base and then with a dialkyl sulfide to form 3α,5-cyclo-6β-benzyloxy-20S-formyl-5α-pregnane, reacting the pregnane with lithium isobutyne-1 under supercooling to form 3α,5-cyclo-6β-benzyloxy-22R-hydroxy-5α-cholest-23-yne, catalytically hydrogenating the cholest-23-yne in the presence of P2-nickel catalyst to form the corresponding cholest23-ene compound, reacting the latter with a peroxide to form (22R,23S,24R)-3α,5-cyclo-6β-benzyloxy-22-hydroxy-23,24-epoxy-5α-cholestane, reacting the epoxy compound with trimethyl aluminum and n-butyl lithium under super-cooling to form 3α,5-cyclo-22R,23R-dihydroxy-6β-benzyloxy-5α-cholest-24-ene, reacting the cholestene with a reagent capable of converting the 22,23-dihydroxyl groups to OR⁴ groups other than the hydroxyl groups to form the corresponding 22,23-di(OR')-cholest-24-ene compound, and thereafter subjecting the latter compound to catalytic hydrogenation to form a 3α,5-cyclo-22,23-di(OR')-cholestan-6β-ol and optionally reacting the resultant 6β-ol compound with an oxidizing agent.

In the above processes, the free hydroxyl group or groups are often protected with the group R' such as an acyl group which can easily split off by hydrolysis. In some cases, the free hydroxyl group or groups can be protected with a tosyl or mesyl group as a sulfonic ester group. For the purpose of protecting the free hydroxyl group, therefore, such sulfonic ester group can be incorporated into the category of acyl groups.

Among the new compounds of the present invention, the compound of the general formula (B) wherein the two radicals R' are combined together to form a isopropylidenedioxy group, i.e. the compound of the formula I-a is one of the useful intermediate products for brassinolide and its analogues and can be used directly for the preparation of the compound of the formula XV-a in one step. Thus, the compound of the formula XV-a which can be converted to brassinolide according to the Ikekawa et al. process can be prepared according to the present invention from the compound of the formula XIII without any difficulty in the operations in less expensive manner as compared with the aforesaid Siddall et al. process.

As compounds similar in structure to the known compound of the formula XV-a, there are two new compounds of the following formulas XV-c and XV-g wherein Ac stands for acetyl group.

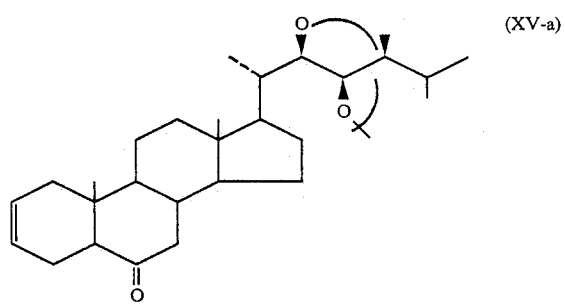

(XV-a)

13

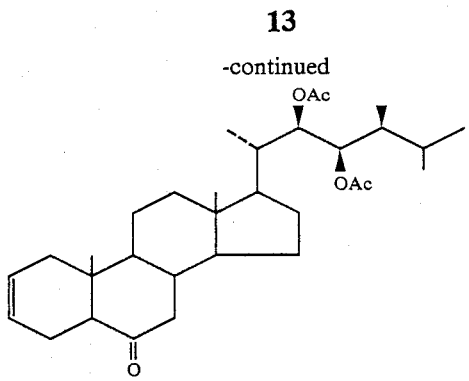

(XV-c)

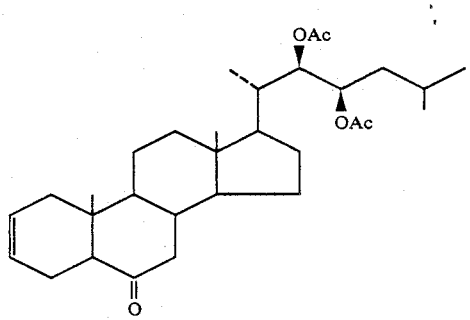

(XV-g)

The new compound of the formula (XV-c) can directly be derived from the new compound of the present invention represented by the formula (I-c) in one step and constitutes an important intermediate for the synthesis of 22,23-diacetylbrassinolide. It is also an intermediate, like the above compound of the formula (XV-a), for the synthesis of brassinolide.

The new compound of the formula (XV-g) can directly be derived from the new compounds of the present invention represented by the formula (I-g) in one step and also constitutes an important intermediate for the synthesis of brassinone.

Accordingly, the new compounds of the present invention represented by the general formula (A) including the 3α,5-cyclo-6-one compounds of the general formula (B) and the 3α,5-cyclo-6β-ol compounds of the general formula (C) are useful as intermediates for brassinolide and its analogues.

The new compounds of the present invention can be prepared from the known starting material or intermediate products for brassinolide or its analogues according to methods known per se.

The routes of preparing the new compounds of the present invention are shown in the following Schemes 2–6, with the process (i) for preparing the compounds of the general formula (D) being shown in Scheme 2, the process (ii) for preparing the compounds of the general formula (D') being shown in Schemes 3 (the latter half of the process) and 6 (the former half of the process), the process (iii) for preparing the compounds of the general formula (B') being shown in Scheme 4 and the process (iv) for preparing the compounds of the formula (D") being shown in Schemes 5 (the latter half of the process) and 6 (the former half of the process):

14

Scheme 2

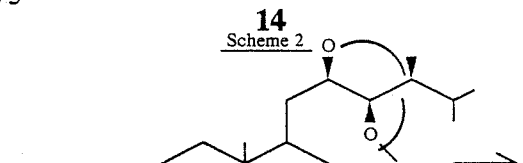

XIII

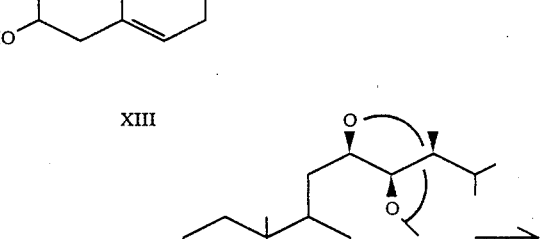

XIV

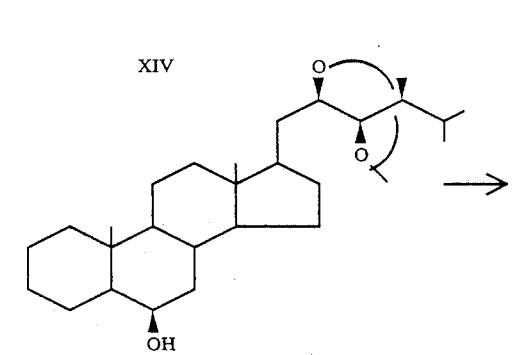

II-a

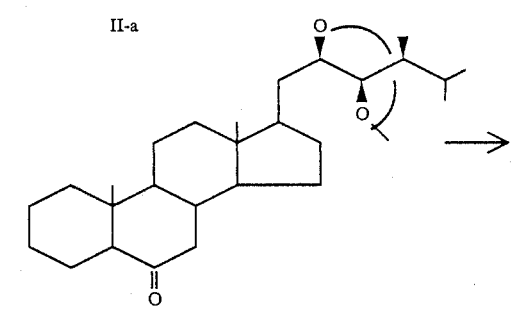

I-a

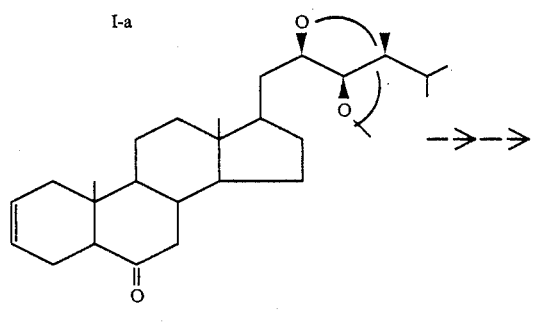

XV-a

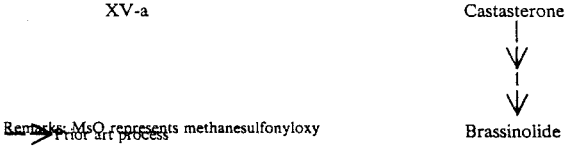

Remarks: MsO represents methanesulfonyloxy

Castasterone

↓

↓

Brassinolide

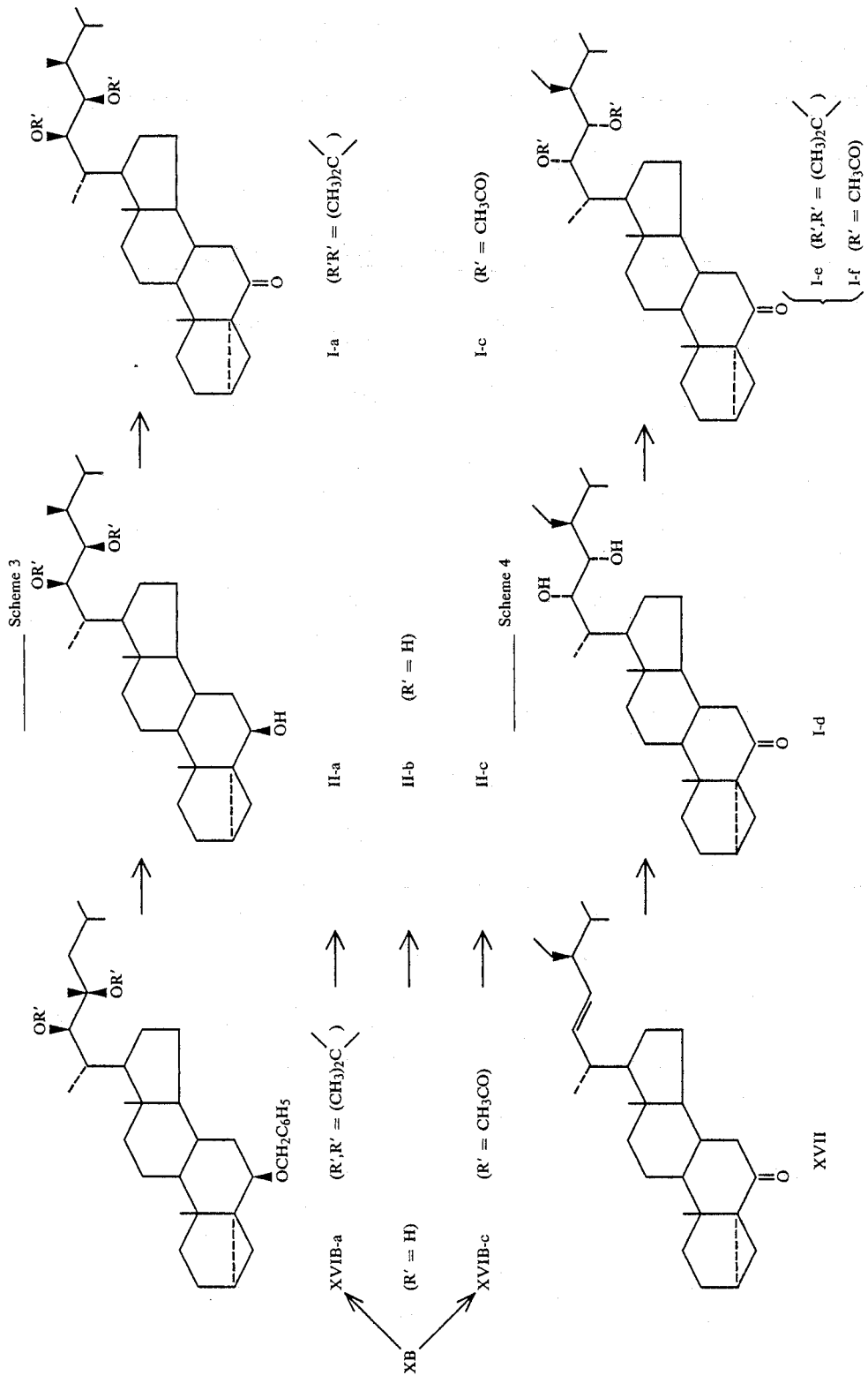

Scheme 5
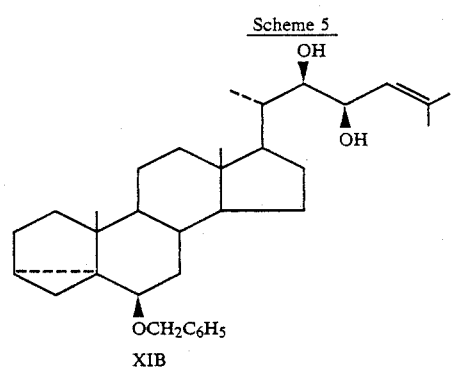
XIB
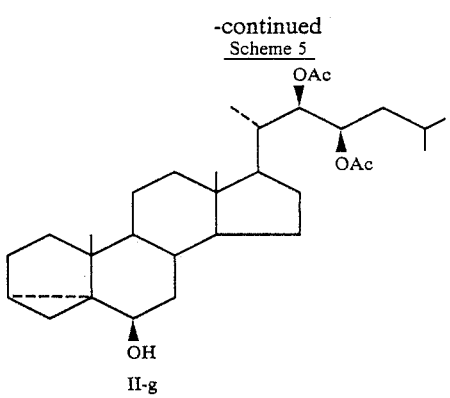
II-g
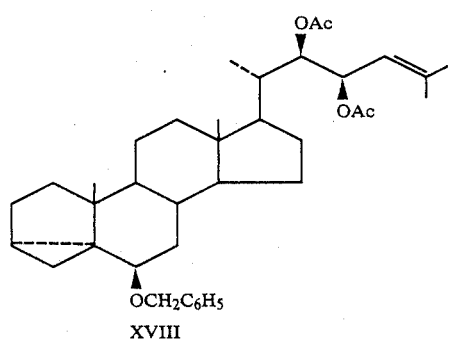
XVIII
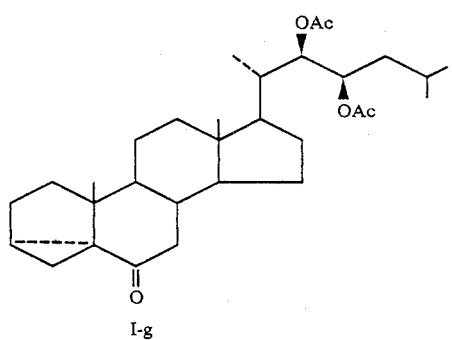
I-g
Remarks: Ac stands for acetyl group.
Scheme 6
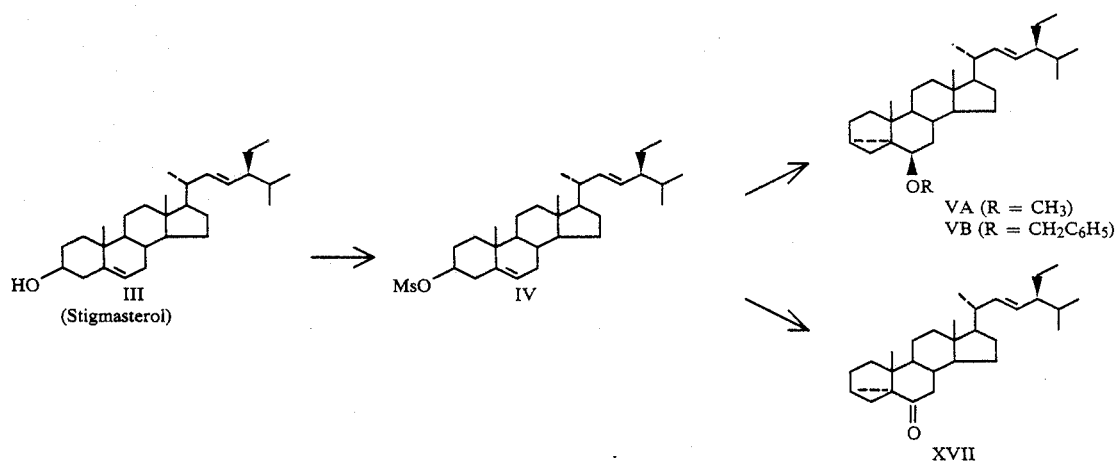
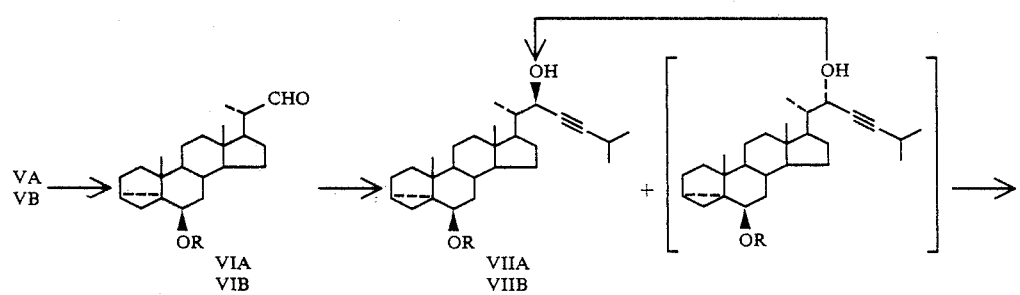

Scheme 6 (continued)

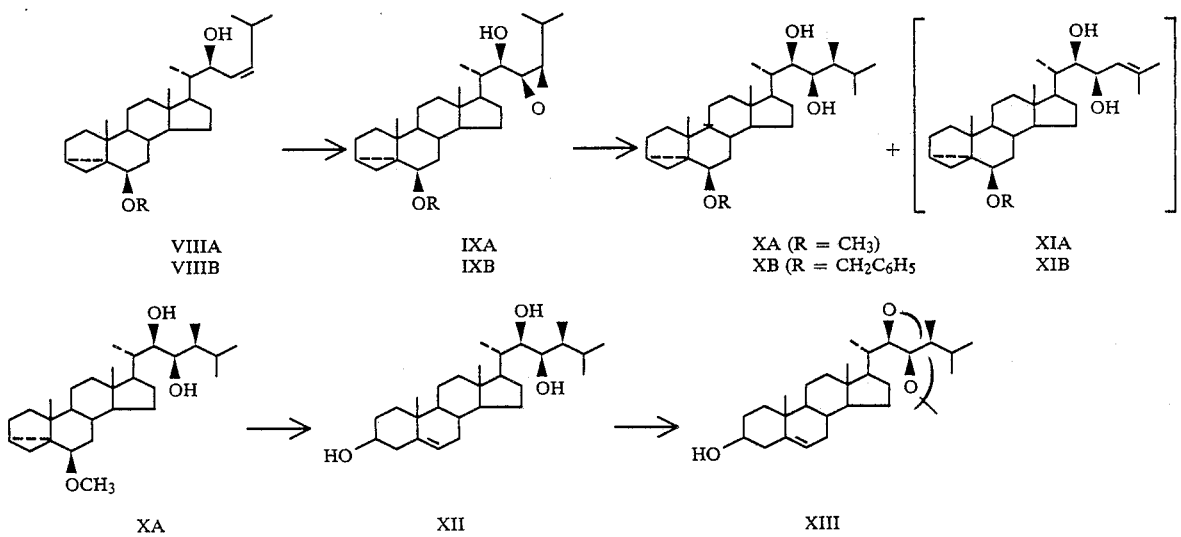

VIIIA / VIIIB → IXA / IXB → XA (R = CH₃) / XB (R = CH₂C₆H₅) + XIA / XIB

XA → XII → XIII

In the process (i) shown in Scheme 2, the compounds of the formulas (XIII), (XIV) and (XV-a) are known except the compounds of this invention represented by the formulas (II-a) and (I-a).

For brevity, the compound of the formula (XIII), for example, will be referred to hereinafter simply as the compound (XIII).

In the process (i), the starting compound (XIII) which can be prepared according to either the known Siddall et al. process or the new process of the present invention in a better yield as shown in Scheme 6 is first mesylated to protect the 3β-free hydroxyl group. The compound (XIII) is dissolved in a proper solvent and a methanesulfonyl halide is added together with an acid-binding agent to the solution. Methyl ethyl ketone or acetone is preferably used as the solvent and a tertiary amine such as triethylamine or pyridine is used as the acid-binding agent. By this reaction (mesylation), the corresponding 3β-mesyloxy compound (XIV) is obtained at a high yield. The compound (XIV) is then dissolved in an aqueous organic solvent such as a mixture of water and a water-miscible inert solvent, e.g. acetone or methyl ethyl ketone and is treated according to the new process of this invention with a weak inorganic base whereby the new compound (II-a) having a specific 3α-5-cyclic structure and 6β-hydroxy group is obtained. Preferable examples of the weak inorganic base include alkali metal carbonates and bicarbonates such as potassium carbonate or bicarbonate and sodium carbonate or bicarbonate. The resultant (22R,23R,24S)3α-5,-cyclo-22,23-isopropylidenedioxy-24-methyl-5α-cholestan-6β-ol (II-a) can optionally be oxidized in a solvent with Jones reagent (CrO₃–H₂SO₄) to prepare the corresponding 6-one compound (I-a), i.e. (22R,23R,24S)-3α,5-cyclo-22,23-isopropylidenedioxy-24-methyl-5α-cholestan-6-one. Illustrative of the solvent used in the oxidation reaction are, for example, a lower alkyl acetate such as ethyl acetate and a ketone such as acetone or methyl ethyl ketone.

The compound (I-a) thus obtained can be converted to the known compound (XV-a) advantageously according to the new isomerization method of the present invention as will be detailed hereinafter with respect to Scheme 7. The compound (XV-a) can be converted in turn to brassinolide via castasterone according to the prior art process.

In comparison with the prior art process as shown in Scheme 1, the process of this invention as shown in Scheme 2 affords the compound of the formula (XV-a) in an approximately same yield but is extremely advantageous and economical since the process of this invention does not require the use of a special reagent diborane which is expensive and cumbersome to handle. Thus, the present invention is of high significance in establishing an industrially advantageous process for synthesizing brassinolide and its analogues from the compound (XIII).

In the process (ii) shown in Schemes 3 and 6, the compounds of this invention represented by the formulas (II-a), (II-b), (II-c), (I-a) and (I-c) can be prepared from the known starting compound stigmasterol (III) through a new route. In these Schemes, the compounds (VIA), (VIB),(VIIA), (VIIB),(VIIIA), (VIIIB), (IXA), (IXB), (XB), (XVIB-a) and (XVIB-c) are new compounds. In these Schemes, acetyl group and acetonide group are given merely as examples for the simplest cases for R' as substituents in 22- and 23-positions.

According to the process (ii), stigmasterol (III) is first mesylated to protect the 3β-free hydroxyl group in such manner that stigmasterol is dissolved in an inert organic solvent such as tetrahydrofuran and a methanesulfonyl halide is added to the solution together with a tertiary amine such as triethylamine as an acid-binding agent to prepare the corresponding 3β-mesylate. This mesylation per se can be carried out in a conventional manner. The 3β-mesyloxy-stigmasterol (IV) is dissolved in a polar solvent, e.g. tetrahydrofuran or DMF and a weak inorganic base and methanol or benzyl alcohol are added as reactants whereby 24S-ethyl-3α,5-cyclo-6β-methyloxy (or benzyloxy)5α-cholest-22-ene (VA or VB) is obtained. The same compounds as mentioned in the preparation of the compound (II-a) in the process (i) can be used as the weak inorganic base. The compound (VA or VB) is then dissolved in a proper solvent such as methylene chloride, and methanol and KHCO₃ or NaHCO₃ are added to the solution. The mixture is then cooled below −60° C. and ozone is blown into the solution and then treated with methyl sulfide. The resultant 3α,5-cyclo-6β-methyloxy (or benzyloxy)-20S-formyl-5α-pregnane (VIA or VIB) is then reacted under super-cooling below −60° C., preferably between −60° C. and −70° C. with lithium isopentyne-1 formed in situ from 1,1-dibromo-3-methyl-1-butene and n-butyl lithium to form (22R)-3α,5-cyclo-6β-methoxy (or benzyloxy)22-hydroxy-5α-cholest-23-yne (VIIA or VIIB) together with its 22S isomer which can be converted to the 22S isomer according to Mitsunobu reaction using triphenyl phosphine, benzoic acid and an azodicarboxylic ester. The compound (VIIA or VIIB) is then hydrogenated in a proper solvent such as an alcohol in the presence of P2-nickel catalyst prepared from nickel acetate, NaBH4 and a diamine to form (22R)-3α,5-cyclo-6β-methoxy (or benzyloxy)-22-hydroxy-5α-cholest-23-ene (VIIIA or VIIIB). This cholest-23-ene compound is then treated under cooling with a peroxide to form the corresponding 23S,24R-epoxide (IXA or IXB) which can be purified by column chromatography on silica gel using ethyl acetate and n-hexane as eluent. The epoxide (IXA or IXB) is then treated under super-cooling (−70° C.) with trimethylaluminum and n-butyl lithium to form (22R,23R,24S)-3α,5-cyclo-6β-methoxy (or benzyloxy)-22,23-dihydroxy-24-methyl-5α-cholestane (XA or XB) which can be purified by column chromatography on silica gel using ethyl acetate/n-hexane. In this case,(22R,23R)-3α,5-cyclo-6β-methoxy (or benzyloxy)-22,23-dihydroxy-5α-cholest 24-ene (XIA or XIB) is obtained as a by-product. The compound (XIA or XIB) can be separated from the compond (XA or XB) by column chromatography on silica gel using ethyl acetate/n-hexane.

The known compound (XA) having 6β-methoxy group obtained in the former half of the new process of this invention as shown in Scheme 6 can then be used in the prior art process for preparing the compound (XIII) which is the starting material for the process (1). More precisely, the compound (XA) is treated with p-toluenesulfonic acid in dioxane according to the prior art process whereby (22R,23R,24S)-3β,22,23-trihydroxy-24-methylcholest-5-ene (XII) is obtained. The compound (XII) is then reacted in an organic solvent such as chloroform with a dialkylketone dialkylacetal such as acetone dimethylacetal and a small amount of p-toluenesulfonic acid to prepare the compound (XIII).

On the other hand, the new compound (XB) having 6β-benzyloxy group obtained in the former half of the new process of this invention as shown in Scheme 6 is then reacted in the latter half of the new process as shown in Scheme 3 with a reagent capable of introducing the desired R³ into the 22- and 23-positions of the end compound.

In case a compound wherein two R³ radicals combined together to form an alkylidene group is to be obtained, the compound (XB) is dissolved in a proper solvent such as chloroform or methylene chloride and reacted with a dialkylketone dialkylacetal such as acetone dimethylacetal in the presence of a small amount of p-toluenesulfonic acid to form the compound (XVIB-a), which is then dissolved in an organic solvent such as ethyl acetate or tetrahydrofuran and subjected to hydrogenolysis in the presence of a hydrogenation catalyst such as Pd-C or Pt black whereby the benzyl group in the 6β-position is split off to form the compound (II-a).

In case a compound wherein each R³ radical is an acyl group is to be obtained, the compound (XB) is dissolved in a proper organic solvent and reacted with an acylating agent in the presence of an acid-binding agent. Thus, the use of a tertiary amine such as pyridine is preferable as the solvent as it has dual functions of a solvent and an acid-binding agent. In case of R³ being acetyl group, the compound (XB) is dissolved in pyridine, and acetic anhydride and N,N-dimethylaminopyridine are added for acetylation.

In case a compound wherein each R³ radical is a silyl group is to be obtained, the compound (XB) is dissolved in an organic solvent such as dimethylformamide, and a proper silylating agent and an acid-binding agent are added. One of the preferable silylating agents is dimethyl t-butyl silyl chloride. A preferable acid-binding agent jointly used with the silylating agent is imidazole.

In case a compound wherein each R³ radical is a carbonyl group or an alkoxycarbonyl group is to be obtained, phosgen or a dialkyl carbonate such as diethyl carbonate can be used in place of the above mentioned acylating agent (R³=carbonyl) or alternatively, an alkoxycarbonyl halide such as t-butoxy-carbonyl chloride widely used in the field of polypeptide chemistry can be used in place of the above mentioned acylating agent in the same manner.

In case a compound wherein each R³ radical is a benzyl group is to be otained, the compound (XB) is dissolved in a polar organic solvent and reacted with sodium hydride and then with a benzyl halide such as benzyl chloride. In this case, a dialkylacylamide such as dimethylformamide, diethylformamide or dimethylacetamide is preferably employed as the polar solvent.

In Scheme 3, only two cases wherein the free hydroxyl groups in the 22- and 23-positions are acetonized (i.e. R' is an alkylidene group) or acetylated (i.e. R' is an acetyl group) are shown as the compounds (XVIB-a) and (XVIB-c), respectively.

The compound (XVIB-c) having desired OR³ groups in the 22- and 23-positions can thus be prepared. As in the case of preparing the compound (II-a), the compound (XVIB-c) is then dissolved in a suitable organic solvent as mentioned above and subjected to hydrogenolysis in the presence of a suitable hydrogenation catalyst as mentioned above whereby the benzyl group in the 6β-position is split off to form the corresponding 6β-hydroxy compound (II-c).

It is also possible to subject the compound (XB) to the catalytic hydrogenolysis in the same manner as described above whereby the corresponding trihydroxyl compound (II-b) can be obtained.

The compounds(II-a and II-c) thus obtained can optionally be oxidized to the corresponding 6-one compounds (I-a and I-c). This oxidation can be carried out by dissolving the compound (II-a or II-c) in a proper organic solvent such as acetone, methyl ethyl ketone or ethyl acetate and treating the compound with Jones reagent (CrO3-H2SO4) under cooling as shown in Schemes 2,3 and 4.

In the process (iii), the known compound (XVII) used as the starting material for preparing the end compounds of the general formula (B') can be prepared from the compound (IV) according to a variant of the method for preparing the compound (VA or VB) followed by oxidation as shown in Scheme 6 [Agric. Biol. Chem. 44, 1211 (1980) referred to]. More precisely, the compound (IV) is refluxed in an aqueous organic solvent such as acetone/water with a weak inorganic base as used in the preparation of the compound (VA or VB) to prepare a compound having the same structure as of the compound (VA or VB) but having the free hydroxyl group in place of OR group. This 6β-hydroxy compound is then oxidized with Jones reagent whereby the 6β-hydroxyl group is converted to oxo group to form the compound (XVII).

The process (iii) is shown in Scheme 4 wherein the compound (XVII) is dissolved in an aqueous organic solvent such as a mixture of tetrahydrofuran and water and is treated with osmium tetraoxide and N-methylmorpholine oxide whereby the 22,23-double bond of the compound (XVII) is attacked to form (22S,23S, 24S)-3α,5-cyclo-22,23-dihydroxy-24-ethyl-5α-cholestan-6-one (I-d). This compound (I-d) can then be reacted optionally with a reagent capable of converting the hydroxyl groups in the 22- and 23-positions to OR' groups other than the hydroxyl group. This reaction itself can be carried as a rule in the same manner as described above with respect to the preparation of the compound (XVIB-a or -c). Thus, the reagent used in this optional reaction can be selected from the various reactants used for converting the hydroxy groups in 22- and 23-positions in the compound (XVIB-a) or (XVIB-c) to the desired OR³ groups.

The compounds of the general formula (B') thus obtained are useful as valuable intermediates for the preparation of S,S-homobrassinolides.

In the process (iv) for preparing the compounds of the general formula (D″) from stigmasterol, a series of the reactions proceed along the route as shown in Schemes 5 and 6. In the process (iv), the former half of the process as shown in Scheme 6 is carried in the same manner as described above with respect to the process (ii), starting with stigmasterol (III). When the compound (IXA or IXB) is reacted in an inert solvent such as n-hexane with trimethylaluminum and n-butyl lithium to obtain the compound (XA or XB) in the process (ii), 3α,5-cyclo-22R, 23R-dihydroxy-6β-methoxy (or benzyloxy)-5α-cholest-22-ene (XIA or XIB) is obtained as a by-product together with the compound (XA or XB). The compound (XIA or XIB) can be separated from the compound (XA or XB) by column chromatography on silica gel using ethyl acetate/n-hexane as eluent. In the latter half of the process (iv) as shown in Scheme 5, the compound (XIB) is reacted with a reagent capable of converting the free hydroxyl groups in the 22- and 23-positions to OR⁴ groups in the same manner as described above with respect to the process (ii) for conversion of the free hydroxyl groups to OR³ groups except for the case of two R³ radicals being combined together to form an alkylidene group. As a mere example, Scheme 5 shows the case of R⁴ being an acetyl group, but R⁴ is not limited only to acetyl group. The resultant compound (XVIII) having the desired OR⁴ groups in the 22- and 23-positions is then dissolved in a suitable organic solvent such as ethyl acetate or tetrahydrofuran and subjected to catalytic hydrogenolysis in the presence of a hydrogenation catalyst such as Pd-C or Pt black under conventional hydrogenating conditions whereby the benzyl group in the 6β-position is split off to obtain 3α,5-cyclo-22R,23R-di(OR⁴)-5α-cholestan-6β-ol (II-g). In the same manner as described above with respect to the conversion of the compound (II-a or II-c) to the compound (I-a, I-c), the compound (II-g) can also be oxidized optionally to the corresponding 6-one compound (I-g). The compound (I-g) thus obtained is a valuable intermediate for the preparation of brassinone (28-norcastasterone).

In addition to the new processes for preparing the compounds of the present invention represented by the general formula (A), a new process for the preparation of the known compound (XIII) has also been found by the present inventors. Although several processes have been reported heretofore as teaching the route for preparing the compound (XIII) from stigmasterol (III), such processes require a number of steps and give a very poor yield of the products. However, the present inventors have found that the known compound (X A) which can easily be converted to the compound (XIII) according to the conventional process can be obtained in a smaller number of steps from the known compound (VI A) in a good yield. According to the new short-circuit process, the known compound (VI A) is treated with 3-methyl-1-butynyl-lithium whereby a new compound (VII A) wherein the ratio of 22R:22S is 3:2 is obtained. The 22R and 22S isomers can be separated by column chromatography on silica gel and the 22S isomer can be converted into the 22R isomer, for example, by the Mitsunobu reaction using triphenylphosphine, a diazocarboxylate and benzoic acid. The resultant 22R isomers of the compound (VII A) are combined and subjected to catalytic hydrogenation in the presence of P2-nickel catalyst followed by epoxidation with a peroxide to afford a new epoxy compound (IXA). This new compound is then treated with trimethylaluminum and n-butyl lithium under strong cooling whereby the known compound (XA) is obtained in an overall yield of 35% [41% in a yield corrected for the recovery of the compound (IXA)]. As the radical R in 6β-position of these compounds in this new process is methyl group, this new process will be referred to hereinafter as the methyl ether process.

On the other hand, the new compound (XB) used as the starting compound in the latter half of the process (ii) as shown in Scheme 3 can be prepared from stigmasterol according to the new process wherein the 6β-hydroxy group of the compound (IV) is first etherified with benzyl alcohol to form 6β-benzyloxy group as shown in Scheme 6. The new compound (VB) having the 6β-benzyloxy group is then converted into the new compound (XB) via the new compounds (VIB), (VIIB),(VIIIB) and (IXB), as described hereinbefore, in a similar manner to the methyl ether process. In this new process, an overall yield of the compound (XB) based on stigmasterol is 19.5% [23.7% in a yield corrected for the recovery of the compound (IXB)]. This new process serves not only to reduce the number of steps in the prior art processes required for preparing brassinolide and its analogues but also to improve various factors in the process, including the yield of products, reaction conditions and labor conditions, so that these merits make the new process attractive from the economical and industrial points of view. This new process will be referred to hereinafter as the benzyl ether process. The benzyl ether process constitutes the former half of the processes (ii) and (iv) of the present invention.

The steroid compounds of the present invention represented by the general formula A, especially the specific formula I-a, I-c, I-d, I-e, I-f and I-g can advantageously be used in the subsequent steps for the preparation of brassinolide and its analogues. The routes for preparing brassinolide and its analogues from the compounds of the present invention are shown in Scheme 7 wherein Ac stands for acetyl group and R″ stands for the group indicated for the particular formulas and wherein the Part (a) relates to the new isomerization step from the compound (I-a) to the known compound (XV-a) according to this invention, the Parts (b) and (c) relate to the same isomerization step from the compounds (I-c) and (I-g) to the new compounds (XV-c) and (XV-g), respectively and to the subsequent new steps for preparing brassinolide and the Part (d) relates to the steps continuing from the Part (b) for the preparation of brassinone.
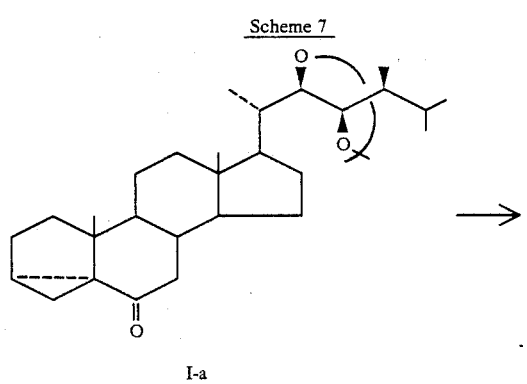
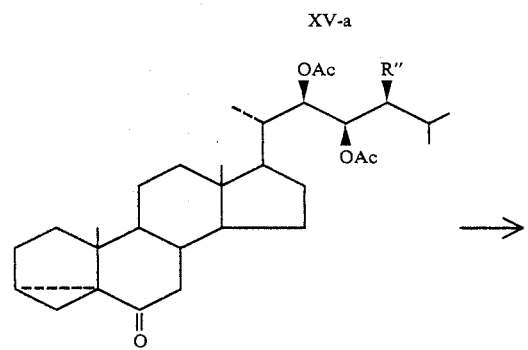
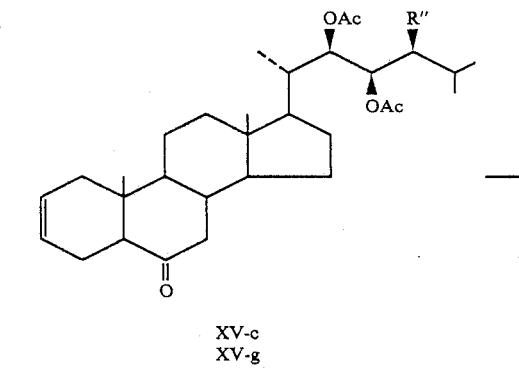
-continued
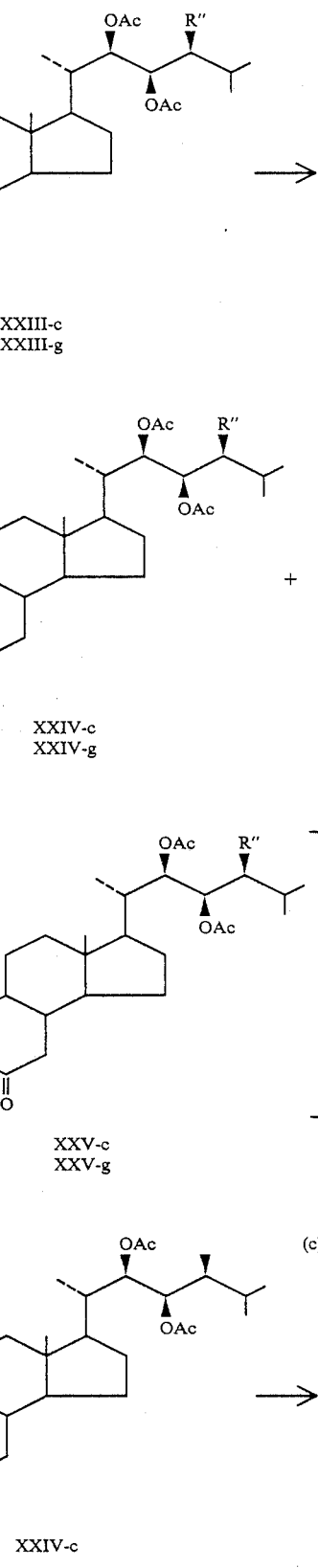

-continued
Scheme 7

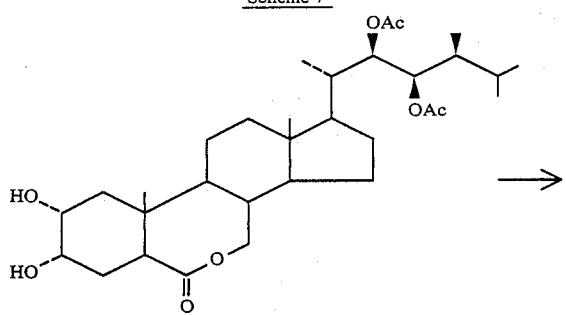

XXVI

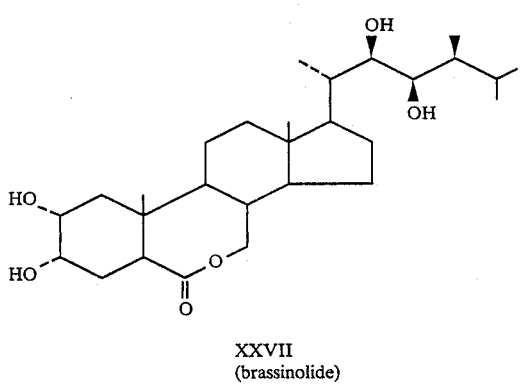

XXVII
(brassinolide)

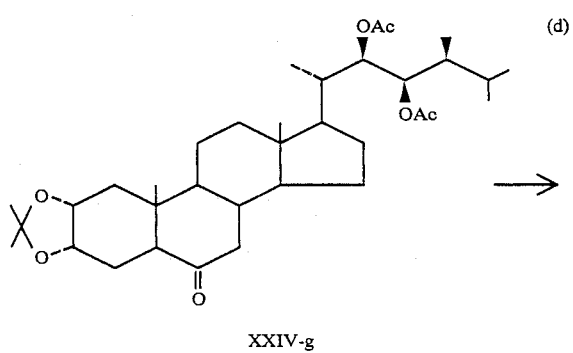

XXIV-g

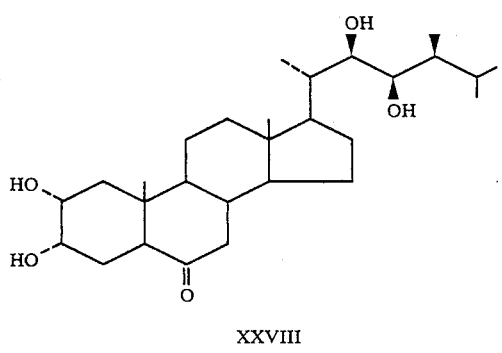

XXVIII

In Part (a) of Scheme 7, the compound (I-a) obtained according to the process (i) is converted into the known compound (XV-a) which is one of the valuable intermediates for the synthesis of brassinolide and is converted thereinto according to the prior art process as shown in Scheme 1.

The isomerization process for converting the compound (I-a) to the known compound (XV-a) has been developed for the first time by the present inventors and is carried out smoothly to afford a better yield of the product. It has surprisingly been found that when the compound (I-a) of this invention is treated in a polar solvent with a metal salt, this compound is efficiently isomerized to the compound (XV-a). Examples of the metal salt in this reaction include lithium bromide, sodium bromide and magnesium bromide, with the lithium bromide being preferable. Illustrative of the polar solvent are, for example, a dialkylformide such as dimethylformamide or diethylformamide and a dialkylacetamide such as dimethylacetamide. In detail, the compound (I-a) is dissolved in such polar solvent and the metal salt and a catalytically small amount of p-toluenesulfonic acid are added to the solution. The mixture is then heated to afford the compound (XV-a) in a good yield. The compound (XV-a) can be converted into brassinolide according to the prior art process, e.g. Ikekawa et al. or Siddall et al. process as described in some detail hereinbefore with respect to the route shown in Scheme 1.

The Parts (b) and (c) show a new route for preparing brassinosteroid from the compound (I-c) or (I-g). In Part (b) constituting the former half of this new route, the compound (I-c) or (I-g) is converted into the compound (XV-c) or (XV-g), respectively, in the same isomerization reaction as described with respect to the compound (I-a). The compound (XV-c) or (XV-g) is then treated in an aqueous organic solvent such as a mixture of water and tetrahydrofuran and/or tert-butanol with osmium tetraoxide and N-methylmorpholine oxide whereby the double bond in the 2,3-positions is opened to yield the corresponding 2,3-dihydroxyl compound (XXIII-c) or (XXIII-g), respectively. This compound is then reacted with a dialkylketone dialkylacetal such as acetone dimethylacetal in the presence of a catalytically small amount of p-toluenesulfonic acid whereby the two isomers (XXIV-c) or (XXIV-g) and (XXV-c) or (XXV-g) of the corresponding 2,3-alkylidenedioxy (isopropylidenedioxy in Scheme 7) compound are obtained, which can be separated from each other by column chromatography on silica gel using ethyl acetate/n-hexane as eluent. The compounds shown in Part (b) are all new compounds. In Part (c), the compound (XXIV-c) is subjected to Bayer-Villiger oxidation whereby an oxa group is introduced into the ring B to form the 7-oxa-B-homo structure and at the same time the alkylidene group in the 2,3-position is split off to give (2R,3S,22R,23R,24S)-2,3-dihydroxy-22,23-diacetoxy-24-methyl-B-homo-7-oxa-5α-cholestan-6-one(XXVI). This product can be converted easily to brassinolide, i.e. (2R,3S,22R,23R,24S)-2,3,22,23-tetrahydroxy-24-methyl-B-homo-7-oxa-5α-cholestan-6-one(XXVIII), by the treatment with a caustic alkali such as sodium or potassium hydroxide in an aqueous alcoholic solution. In Part (c), all the compounds except brassinolide are new compounds.

In Part (d) showing the route for preparing brassinone from the compound (XXIV-g) which is in turn derived from the compound (XV-g), the compound (XXIV-g) is first subjected to an alkaline solvolysis conducted in an aqueous alcoholic solution with a caustic alkali such as sodium or potassium hydroxide to split off the acyl group in the 22- and 23-positions and then to an acidic solvolysis conducted in an aqueous strong acid such as an aqueous solution of a mineral acid, e.g. HCl to split off the alkylidene group in 2,3-position whereby brassinone (or 28-norcastasterone)(XXVIII) is obtained.

According to the present invention, various remarkable improvements can be made in the prior art processes for preparing brassinosteroids. Firstly, the present invention provides a new process for preparing the compound (XV-a) from the compound (XIII) which can be carried out economically on an industrial scale and involves a specific new isomerization step from the compound (I-a) to the compound (XV-a). Secondly, the present invention provides plural new processes for preparing brassinosteroids from stigmasterol in a smaller number of steps or in a better yield. In this connection, the present invention provides the new methyl ether process using the 6β-methoxy compounds for preparing the compound (XA) from stigmasterol through the compounds (VA)-(IXA) as well as the new benzyl ether process using the 6β-benzyloxy compounds for preparing the compound (II-a, II-b or II-c) from stigmasterol through the new compounds(VB)-(XVIB-a or XVIB-c). In case of the methyl ether process, the yield of the compound (XA) is as high as 35% based on the compound (VIA) through 4 steps. In case of the benzyl ether process, the compound (XV-a) can be prepared in a total yield of 14.5% from stigmasterol. In case the compound (II-c) is used in place of the compound (II-a), the new compound (XV-c) can be obtained according to the benzyl ether process from stigmasterol in a total yield of 15%, requiring only 11 steps. According to the present invention, the yield of brassinolide based on stigmasterol is 7.8% through 15 steps. This yield is quite surprising since the maximum yield reported hitherto is about 3% based on stigmasterol in Mori et al. process involving 16 steps. Thus, the process of this invention as a whole is advantageous as compared with the prior art processes and is easily operable on an industrial scale without any difficulty.

The preparation of the new compounds of this invention will now be illustrated in more detail by the following examples wherein the compound numbers in parenthesis annexed to the compounds all correspond to those as shown in the relevant Schemes given above.

EXAMPLE 1

(22R,23R,24S)-3α,5-Cyclo-6β-methoxy-22,23-dihydroxy-24-methyl-5α-cholestane (XA)

10.26 g of 1,1-dibromo-3-methyl-1-butene and 180 ml of tetrahydrofuran (THF) are cooled to −65° C. under an atmosphere of nitrogen, and 50 ml of a 1.8N n-butyl lithium solution in hexane is added dropwise to the mixture at −65°−−60° C. After the dropwise addition, the whole reaction mixture is stirred for a 30 minutes, during which the temperature rises from −60° C. to −40° C. The mixture is then cooled to −70° C., and a solution of 10.34 g of 3α,5-cyclo-62-methoxy-20S-formyl-5α-pregnane (VI A) in 90 ml of THF is added dropwise at −70°−−68° C. After the dropwise addition, the reaction mixture is stirred for 1 hour at −72°−−68° C. and then for 2 hours during which the temperature rises from −70° C. to 0° C. To the reaction product are added a saturated aqueous ammonium chloride solution and ether, and then water. The mixture is then phase separated to collect the organic layer. The organic layer is washed with 5% saline and saturated saline, dried over anhydrous magnesium sulfate and concentrated in vacuo. The concentrate is applied to 300 g of silica gel No. 7734 (Merck) and eluted with AcOEt/n-hexane (=1/10-⅓) to obtain 6.10 g of (22R)-3α,5-cyclo-6β-methoxy-22-hydroxy-5α-cholest-23-yne (VII A) (m.p. 124°-125° C.) and 4.49 g of (22S)-3α,5-cyclo-68-methoxy-22-hydroxy-5α-cholest-23-yne (as an amorphous solid). 4.20 g of the 22S isomer is dissolved in 42 ml of THF and 3.94 g of triphenylphosphine and 1.84 g of benzoic acid are added to the solution. After cooling the mixture to 5° C., 2.30 ml of ethyl azodicarboxylate is added dropwise at 5°-10° C. After the dropwise addition, the mixture was stirred for 30 minutes. 120 ml of methanol and 5.52 g of anhydrous potassium carbonate powder are further added and stirred for 2 hours at 50°-60° C. The reaction solution is concentrated in vacuo and phase separated, after addition of ethyl acetate and water, to collect the organic layer, which is then washed with water, dried over MgSO₄ and concentrated in vacuo. The concentrate is applied to 200 g of silica gel and eluted with AcOEt/benzene (=1/100- 1/50) to obtain 3.25 g of 22R isomer (VII A).

Separately, 1.0 g of nickel acetate is dissolved in 20 ml of 95% ethanol, and 8 ml of a 1M ethanolic solution of NaBH₄ is added dropwise to the solution. After addition of 0.54 ml of ethylenediamine, 8.55 g of the 22R isomer (VII A) and 80 ml of ethanol are added to the mixture. After establishing an atmosphere of hydrogen in the reaction system, catalytic reduction is carried out. After this reduction reaction, 100 ml of ether and 2 g of celite (a filter aid) are added and the mixture is filtered. The filtrate is concentrated in vacuo to dryness. Ether and water are added to the residue and the mixture is phase separated to collect the organic layer, which is then washed with water, dried over MgSO₄ and concentrated in vacuo to obtain 8.50 g of (22R)-3α,5-cyclo-6β-methoxy-22-hydroxy-5α-cholest-23-ene (VIII A) as an amorphous solid.

This product is dissolved in 400 ml of methylene chloride and the solution is cooled to 5° C. 8.5 g of m-chloroperbenzoic acid (P=88.3%) is added and the mixture is stirred at 3°-5° C. for 2.5 hours. After adding 200 ml of a 0.5N aqueous caustic soda solution, the reaction mixture is phase separated to collect the organic phase, which is then washed with water, dried over MgSO₄ and concentrated in vacuo. The residue is purified on a column of 200 g of solica gel with AcOEt/n-hexane (=1/6-⅓) to obtain 8.0 g of (22R,23S,24R)-3α,5-cyclo-6β-methoxy-22-hydroxy-23,24-epoxy-5α-cholestane (IX A) as an amorphous solid.

A 4.31 g portion of this product is dissolved in 500 ml of n-hexane and the solution is cooled to −70° C. while establishing an atmosphere of nitrogen in the reaction system. 50 ml of a 19% solution of trimethyl aluminum in hexane and 6 ml of a 15% solution of n-butyl lithium in hexane are added, and the mixture is stirred for 1 hour at −70° C. and for a 4 hours, during which the temperature rises from −70° C. to +10° C. After cooling to −40° C., methanol is added to decompose the trimethyl aluminum, and ether and a 1N aqueous caustic soda solution are then added. The resultant mixture is phase separated to collect the organic layer, which is then washed with water, dried over MgSO₄ and concentrated in vacuo. The residue is applied to 200 g of silica gel and eluted with AcOEt/n-hexane (=1/5-⅓) to recover 612 mg of the starting material (IX A) and to obtain 2.256 g of the desired product (X A) (as an amorphous solid).

NMR (200 MHz)δ: 0.43 (1H, q), 0.65 (1H, t), 2.78 (1H, s), 3.34 (3H, s), 3.6 (1H, m), 3.75 (1H, m).

EXAMPLE 2

(22R,23R,24S)-3α,5-Cyclo-22,23-isopropylidenedioxy-24-methyl-5α-cholestan-6β-ol (II-a)

2,234 mg of the compound (XA) is dissolved in 100 ml of dioxane, and 40 ml of water and 100 mg of p-toluenesulfonic acid are added to the solution. The mixture is stirred at 100° C. for 1 hour. The reaction mixture is then concentrated in vacuo, and water and CHCl$_3$ are added to the residue. The mixture is phase separated to collect the organic phase, which is then washed with an aqueous sodium bicarbonate solution and dried over MgSO$_4$. To the resultant mixture are added 1.0 ml of acetone dimethyl acetal and 50 mg of p-toluenesulfonic acid, and the mixture is stirred for 1 hour. The reaction mixture is concentrated in vacuo to dryness to obtain crude compound(XIII). This product is dissolved in 50 ml of methyl ethyl ketone, and the solution, after addition of 1.75 ml of triethylamine, is cooled to 5° C. 0.78 ml of mesyl chloride is added dropwise and the mixture is stirred for 1 hour. After addition of 10 ml of 15% saline, the reaction mixture is phase separated to collect the organic layer, which is then washed successively with 5 ml of 15% saline +5 ml of 1N hydrochloric acid, 15% saline and water. 15 ml of water and 1.25 g of KHCO$_3$ are added to the resultant organic layer, and the mixture is stirred at 50°-60° C. for 16 hours. The reaction mixture is phase separated to collect the organic layer, which is then washed with 15% saline and saturated saline, dried over MgSO$_4$ and concentrated in vacuo to dryness. The residue is applied to 100 g of silica gel and eluted with AcOEt/benzene (=1/50-1/10) to obtain 1,797 mg of (22R,23R,24S)-3α,5-cyclo-22,23-isopropylidenedioxy-24-methyl-5α-cholestan-6β-ol (II-a). m.p. 187°-189° C. (recrystallized from MeOH).

NMR (200 MHz)δ: 0.30 (1H, q), 0.53 (1H, t), 3.29 (1H, s), 3.77 (1H, q), 3.89 (1H, d).

There is also recovered 496 mg of (22R,23R,24S)-22,23-isopropylidenedioxy-24-methyl-cholest-5-en-3-ol (XIII).

EXAMPLE 3

(22R,23R,24S)-3α,5-Cyclo-22,23-isopropylidenedioxy-24-methyl-5α-cholestan-6-one (I-a)

1,418 mg of (22R,23R,24S)-3α,5-cyclo-22,23-isopropylidenedioxy-24-methyl-5α-cholestan-6β-ol(II-a) is dissolved in a mixture of 30 ml of acetone and 30 ml of AcOEt and the solution is cooled to 5° C. To the solution is added dropwise, with stirring, 1.2 ml of Jones reagent. After a further 30 minutes of stirring at 5° C., the whole reaction mixture is poured into 100 ml of cold water. After adding 100 ml of AcOEt, the mixture is phase separated to collect the organic layer, which is then washed successively with water, an aqueous sodium carbonate and saline in that order, dried over MgSO$_4$ and concentrated in vacuo to dryness. There is obtained 1,342 mg of (22R,23R,24S)-3α,5-cyclo-22,23-isopropylidenedioxy-24-methyl-5α-cholestan-6-one (I-a).

Although this product may be directly used in the subsequent step, a purified product of m.p. 159°-161° C. can be obtained by recrystallization from AcOEt.

NMR (200 MHz)δ: 2.43 (1H, m), 3.77 (1H, q), 3.88 (1H, d). EI/MS m/e: 471, 455, 399, 395, 355, 171, 142, 99.

EXAMPLE 4

(22R,23R,24S)-22,23-Isopropylidenedioxy-24-methyl-5α-cholest-2-en-6-one (XV-a)

1,177 mg of the crude product (I-a) obtained in Example 3 is dissolved in 10 ml of N,N-dimethyl-formamide (DMF). After adding 48 mg of p-toluenesulfonic acid and 132 mg of lithium bromide, the mixture is heated under reflux for 2 hours at 155°-157° C. The reaction mixture is then poured into ice-cold water, and the mixture is extracted with AcOEt. The organic layer is washed successively with water, an aqueous sodium bicarbonate solution and saline in that order, dried over MgSO$_4$ and concentrated in vacuo to dryness. The residue is applied to 100 g of silica gel and eluted with AcOEt/benzene (=1/100-1/50) to obtain 932 mg of the compound (XV-a). m.p. 236°-238° C. (recrystallized from MeOH).

NMR (200 MHz)δ: 3.77 (1H, q), 3.88 (1H, d), 5.61 (1H, m), 5.74 (1H, m).

EXAMPLE 5

(22R,23R,24S)-3α,5-Cyclo-6β-benzyloxy-22,23-dihydroxy-24-methyl-5α-cholestane (X B)

100 ml of THF and 9.8 ml of triethylamine are added to 20.7 g of stigmasterol and the mixture is cooled to 5° C. 5.05 ml of methanesulfonylchloride is added dropwise at 4°-8° C. to the mixture. After stirring for 1 hour, 100 ml of benzylalcohol and 7.95 g of anhydrous sodium carbonate powder are added and the mixture is stirred at 50°-60° C. for 25 hours. After further adding AcOEt and water, the reaction mixture is phase separated to collect the organic layer, which is then washed with water, concentrated in vacuo and distilled in vacuo at 1 Torr to recover the benzyl alcohol. The residue is applied to 250 g of silica gel and eluted with benzene/n-hexane (=¼-⅓) to obtain 16.47 g of 24S-ethyl-3α,5-cyclo-6β-benzyloxy-5α-cholest-22E-ene (V B).

NMR shows a benzene content of 4%, and the yield corrected for the purity is 62.9%.

16.47 g compound (V B) is dissolved in 250 ml of methylene chloride, and 125 ml of methanol and 16 g of sodium bicarbonate are added. After cooling to −70° C., ozone is bubbled into the solution until the reaction mixture turns blue. Subsequently, gaseous nitrogen is bubbled thereinto to remove excess ozone, and 20 ml of dimethyl sulfide is added. After stirring for a 3 hours, during which the temperature rises from −60° C. to −20° C., the mixture is allowed to stand overnight in a refrigerator (at −25° C.). Water is added to the reaction mixture and the phases are separated to collect the methylene chloride layer, which is then washed with 2% saline and saturated saline, dried over MgSO$_4$ and concentrated in vacuo. The residue is purified on a column of 250 g of silica gel with AcOEt/n-hexane (=1/15) to obtain 11.04 g of 3α,5-cyclo-6β-benzyloxy-20S-formyl-5α-pregnane (VI A). Purity (NMR): 92%; yield: 76.8%.

6.84 g of 1,1-bromo-3-methyl-1-butene and 120 ml of THF are cooled to −65° C. under an atmosphere of nitrogen. 34 ml of a 1.8 N solution of n-butyl lithium in hexane is added dropwise at −65° −60° C. After the dropwise addition, stirring is applied for a 30 minutes, during which the temperature rises from −60° C. to −40°. After cooling the whole reaction mixture to −70° C., a solution of 9.14 g of 3α,5-cyclo-6β-benzyloxy-20S-formyl-5α-pregnane (VI B) in 60 ml of THF is added dropwise at −70°−68° C. After the dropwise addition, the mixture is stirred for 1 hour at −72°−68° C., and then for a 2 hours, during which the temperature rises from −70° C. to −0° C. To the reaction mixture are added a saturated aqueous ammonium chloride solution and ether. After further addition of water, the phases are separated to collect the organic layer. The organic layer is washed with 5% saline and saturated saline, dried over MgSO$_4$ and concentrated in vacuo. The residue is applied to 200 g of silica gel and eluted with AcOEt/n-hexane (=1/10) to obtain 4.76 g of (22R)-3α,5-cyclo-6β-benzyloxy-22-hydroxy-5α-cholest-23-yne (VII B)(m.p. 155°–156° C.) and 3.62 g of (22S)-3α,5-cyclo-6β-benzyloxy-22-hydroxy-5α-cholest-23-yne (as an amorphous solid). This 22S isomer is converted, by means of Mitsunobu reaction, into the 22R isomer (VII B) in a yield of 72.6%.

8.0 g of the above 22R isomer (VII B) is subjected to catalytic reduction over a P2-Ni catalyst prepared in ethanol in the same manner as in Example 1, epoxidation with m-chloroperoxybenzoic acid, and purification by column chromatography to give 7.58 g of (22R,23S,24R)-3α,5-cyclo-6β-benzyloxy-22-hydroxy-23,24-epoxy-5α-cholestane (IX B) as an amorphous solid.

5.07 g of the compound (IX B) is dissolved in 500 ml of n-hexane and an atmosphere of nitrogen is established in the reaction system. After cooling to −70° C., 50 ml of a 19% solution of trimethyl aluminum in hexane and 6 ml of a 15% solution of n-butyl lithium in hexane are added to the solution. The mixture is stirred for 1 hour at −70° C., and the for a 4 hours, during which the temperature rises from −70° C. to +10° C. It is then cooled to −40° C. and methanol is added to decompose the trimethyl aluminum. After adding ether and a 1N aqueous caustic soda solution, the phases are separated to collect the organic layer, which is then washed with water, dried over MgSO$_4$ and concentrated in vacuo. The residue is applied to 200 g of silica gel and eluted with AcOEt/n-hexane (=1/5 - ⅓) to obtain the following:

| Starting material (IX B) | 0.89 g |
| Desired product (X B) | 3.05 g |
| Byproduct (XI B) | 0.56 g |

Compound X B: NMR (200 MHz) δ: 0.39 (1H, q), 0.66 (1H, t), 3.00 (1H, b.s), 3.6 (1H, m), 3.75 (1H, m), 4.60 (2H, q), 7.38 (5H, d).
EI/MS m/e: 522, 431, 422, 414, 330, 313, 91.

EXAMPLE 6

(22R,23R,24S)-3α,5-Cyclo-22,23-isopropylidenedioxy-24-methyl-5α-cholestan-6-one (I-a)

2.80 g of (22R,23R,24S)-3α,5-cyclo-6β-benzyloxy-22,23-dihydroxy-24-methyl-5α-cholestane (X B) is dissolved in 60 ml of AcOEt, and 1.4 ml of acetone dimethyl acetal and 140 mg of toluenesulfonic acid are added to the solution. The mixture is stirred for 1 hour. An aqueous sodium bicarbonate solution is added to the reaction mixture and the phases are separated to collect the organic layer. The organic layer is dried over MgSO$_4$ and concentrated in vacuo to obtain crude (22R,23R,24S)-3α,5-cyclo-6β-benzyloxy-22,23-isopropylidenedioxy-24-methyl-5α-cholestane (XVI B-a). This product is dissolved in 60 ml of AcOEt and the solution is subjected to catalytic reduction using a 5% Pd/C catalyst. The reaction mixture is checked by TLC to ascertain the exhaustion of the starting material, and the catalyst is filtered off. (Although the filtrate, upon concentration to dryness, gives the compound II-a, it is used here directly in the subsequent step.) The filtrate is cooled to 5° C., and 1.7 ml of Jones reagent is added dropwise. After the dropwise addition, the mixture is stirred for 1 hour. The reaction mixture is washed successively with water, an aqueous sodium bicarbonate solution and saline, dried over MgSO$_4$ and concentrated in vacuo to dryness. The residue is applied to 100 g of silica gel and eluted with AcOEt/benzene (=1/30 - 1/15) to obtain 2.26 g of the compound (I-a). This product gives the compound (I-a) of m.p. 159°–161° C. when recrystallized from AcOEt.

EXAMPLE 7

(22R,23R,24S)-3α,5-Cyclo-22,23-isopropylidenedioxy-24-methyl-5α-cholestan-6β-ol (II-a)

252 mg of the compound (X B) is dissolved in 30 ml of AcOEt, and 126 mg of a 5% Pd/C catalyst (50% wet product) is added to the solution to effect catalytic reduction under an atmosphere of hydrogen. After ascertaining the disappearance of the starting material by TLC, the catalyst is filtered off and the filtrate is concentrated to dryness to afford 200 mg of (22R,23R,24S)-3α,5-cyclo-22,23-dihydroxy-24-methyl-5α-cholestan-6β-ol (II-b) which gives almost one spot in TLC. The product is dissolved in 20 ml of chloroform, and 10 mg of p-toluenesulfonic acid and 0.10 ml of acetone dimethyl acetal are added. After stirring at 10° C. for 30 minutes, the mixture is washed with an aqueous sodium bicarbonate, dried over MgSO$_4$ and concentrated in vacuo to dryness to give crude compound (II-a).

Although this product may be directly used in the subsequent step, a purified product (II-a) of m.p. 187°–189° C. can be obtained by recrystallization from methanol.

EXAMPLE 8

(22R,23R,24S)-3α,5-Cyclo-22,23-diacetoxy-24-methyl-5α-cholestan-6-one (I-c)

2.092 g of (22R,23R,24S)-3α,5-cyclo-6β-benzyloxy-22,23-dihydroxy-24-methyl-5α-cholestane (X B) is dissolved in 10 ml of pyridine and the solution is cooled to 5° C. 1.89 ml of acetic anhydride and 40 mg of N,N-dimethylaminopyridine are added, and the mixture is stirred at 5° C. for 1 hour and then at room temperature for 16 hours. AcOEt and water are added, and the AcOEt layer is separated and washed successively with cold 1N hydrochloric acid, water, an aqueous sodium bicarbonate and saline. It is then dried over MgSO$_4$ and concentrated in vacuo to dryness to give 2.29 g of (22R,23R,24S)-3α,5-cyclo-6β-benzyloxy-22,23-diacetoxy-24-methyl-5α-cholestane (XVI B-c) as an amorphous solid.

NMR (60 MHz) δ: 1.98 (6H, d), 2.95 (1H, b.s.), 4.55 (2H, q), 5.25 (2H, q), 7.3 (5H, d).

The compound (XVI B-c) is dissolved in 80 ml of AcOEt, and 0.5 g of 5% Pd/C is added to the solution to effect catalytic hydrogenation under atmospheric pressure at room temperature. After TLC checking to ascertain the disappearance of the starting material, the catalyst is filtered off and the filtrate is concentrated in vacuo to dryness to give 2.18 g of (22R,23R,24S)-3α,5- cyclo-22,23-diacetoxy-24-methyl-5α-cholestan-6β-ol (II-c) as an amorphous solid.

NMR (60 MHz) δ: 1.98 (6H, d), 3.23 (1H, b.s), 5.25 (2H, q).

2.18 g of the compound (II-c) is dissolved in 50 ml of AcOEt and after cooling to 5° C., 1.25 ml of Jones reagent is added dropwise. The resultant mixture is stirred at 5° C. for 1 hour and the reaction mixture is washed successively with water, an aqueous sodium bicarbonate solution and saline in that order, dried over MgSO$_4$ and then concentrated in vacuo to dryness to give 2.06 g of crude (22R,23R,24S)-3α,5-cyclo-22,23-diacetoxy-24-methyl-5α-cholestan-6-one (I-c). A portion of this product is recrystallized from AcOEt-methanol to give a purified product (I-c) of m.p. 173.5°–174.5° C.

EXAMPLE 9

(22R,23R,24S)-22,23-Diacetoxy-24-methyl-5α-cholest-2-en-6-one (XV-c)

1.86 g of the crude compound (I-c) is dissolved in 16 ml of DMF, and 68 mg of p-toluenesulfonic acid and 190 mg of lithium bromide are added. The mixture is heated under reflux at 155°–157° C. for 1.5 hours. The reaction mixture is poured into ice-cold water and extracted with AcOEt. The AcOEt layer is washed successively with water, an aqueous sodium bicarbonate solution and saline in that order, dried over MgSO$_4$ and concentrated in vacuo. The residue is then applied to 80 g of silica gel and eluted with AcOEt/benzene (=1/25 - 1/15) to obtain 1.37 g of (22R,23R,24S)-22,23-diacetoxy-24-methyl-5α-cholest-2-en-6-one (XV-c). The product is suspended in methanol for purification, whereby a purified product (XV-c) of m.p. 210°–213° C. is obtained. NMR (200 MHz) δ: 2.02 (3H, s), 2.04 (3H, s), 5.21 (1H, d), 5.38 (1H, d), 5.56–5.85 (2H, m).

EXAMPLE 10

Brassinolide (XXVII)

1.32 g of (22R,23R,24S)-22,23-diacetoxy-24-methyl-5α-cholest-2-en-6-one (XV-c) is dissolved in a solution consisting of 50 ml of tert-butanol, 15 ml of THF and 5 ml of water. 1.0 g of N-methylmorpholine oxide and then 32 mg of osmium tetroxide are added, and the mixture is stirred at room temperature for 8 hours. After adding an aqueous sodium sulfite solution, the mixture is further stirred for 30 minutes. AcOEt and water are added and the phases are separated. The AcOEt layer is washed with 1N HCl, water and an aqueous sodium bicarbonate solution, dried over MgSO$_4$ and concentrated in vacuo to dryness to obtain compound (XXIII-c). This product is dissolved in 60 ml of chloroform, and 0.75 ml of acetone dimethyl acetal and 50 mg of p-toluenesulfonic acid are added. After stirring at room temperature for 1 hour, an aqueous sodium bicarbonate solution is added, and the chloroform layer is collected, dried over MgSO$_4$ and concentrated in vacuo to dryness. The residue is purified on a column of 50 g of silica gel with AcOEt/n-hexane (=⅓- ½) to obtain 1.07 g of (2R,3S,22R,23R,24S)-2,3-isopropylidenedioxy-22,23-diacetoxy-24-methyl-5α-cholestan-6-one (XXIV-c), m.p. 181.0°–181.5° C.

720 mg of the compound (XXIV-c) is dissolved in 25 ml of methylene chloride, and a solution of trifluoroperacetic acid in methylene chloride, prepared from 3 g of Na$_2$HPO$_4$ powder and 1.66 ml of trifluoroacetic anhydride, is added. The mixture is stirred for a 3 hours, during which the temperature rises from 0° to 20° C. Water and CH$_2$Cl$_2$ are added to the reaction mixture and the phases are separated. The CH$_2$Cl$_2$ layer is washed with water and an aqueous sodium bicarbonate solution, dried over MgSO$_4$ and concentrated to dryness to obtain 700 mg of crude (2R,3S,22R,23R,24S)-2,3-dihydroxy-22,23-diacetoxy-24-methyl-β-homo-7-oxa-5α-cholestan-6-one (XXVI). To this product are added 50 ml of methanol, 5 ml of water and 1.5 g of caustic soda, and the mixture is heated under reflux for 2 hours. The reaction mixture is cooled and, after hydrochloric acid is added to adjust the pH to 1, stirred at room temperature for 1 hour. 100 ml of water is added and the mixture is stirred. The crystals formed are collected by filtration to obtain 550 mg of crude brassinolide (XXVII) which, upon recrystallization from methanol, gave brassinolide as needles, m.p. 274°–278° C.

EXAMPLE 11

(22S,23S,24S)-22,23-Isopropylidenedioxy-24-ethyl-5α-cholest-2-en-6-one (XV-e)

80 ml of THF, 20 ml of tert-butanol and 10 ml of water are added to 4.11 g of 3α,5-cyclo-24S-ethyl-5α-cholest-22E-en-6-one (XVII), and 4 g of N-methylmorpholine oxide on 200 mg of osmium tetroxide are added with stirring. The mixture is stirred at room temperature for 3 days. An aqueous sodium hydrosulfite solution is then added and after stirring for 30 minutes AcOEt and water are added and the phases are separated. The resultant organic layer is washed with 1N hydrochloric acid, water and saline, dried over MgSO$_4$ and concentrated in vacuo to dryness. The residue is applied in chloroform to 200 g of silica gel and eluted with acetone/chloroform (=1/20) to obtain 3.66 g of (22S,23S,24S)-3α,5-cyclo-22,23dihydroxy-24-ethyl-5α-cholestan-6-one (I-d), which, upon recrystallization from AcOEt, gives needles, m.p. 162°–167° C.

890 mg of the compound (I-d) is dissolved in 20 ml of chloroform, and 0.50 ml of acetone dimethyl acetal and 40 mg of p-toluenesulfonic acid are added. The mixture is stirred at 15° C. for 30 minutes. The reaction mixture is washed with an aqueous sodium bicarbonate solution, dried over MgSO$_4$ and concentrated in vacuo to dryness to obtain 956 mg of (22S,23S, 24S)-3α,5-cyclo-22,23-isopropylidenedioxy-24-ethyl-5α-cholestan-6-one (I-e), which, upon recrystallization from methanol, gives the compound (I-e), m.p. 131°–132° C.

478 mg of the crude compound (I-e) is dissolved in 5 mg of DMF, and 19 mg of p-toluenesulfonic acid and 53 mg of lithium bromide are added. The mixture is stirred at 155°–157° C. for 2 hours. It is then poured into water and AcOEt, and the AcOEt layer is washed with water, dried over MgSO$_4$ and concentrated in vacuo. The residue is applied to 20 g of silica gel and eluted with AcOEt/benzene (=1/100 - 1/50) to obtain 367 mg of (22S,23S,24S)-22,23-isopropylidenedioxy-24-ethyl-5α-cholest-2-en-6-one (XV-e) as a single spot portion. Purification of the product from methanol gives a pure product of m.p. 163°–166° C.

EXAMPLE 12

(22S,23S,24S)-22,23-Diacetoxy-24-ethyl-5α-cholest-2-en-6-one (XV-f)

10 ml of pyridine is added to 890 mg of the compound (I-d) obtained in Example 11, and the mixture is cooled to 5° C. 0.95 ml of acetic anhydride and 20 mg of N,N-dimethyl-4-aminopyridine are added and the mixture is stirred overnight at room temperature. The reaction mixture is poured into AcOEt and water, and the organic layer is washed successively with 1N HCl, water, an aqueous sodium bicarbonate and saline, dried over MgSO₄ and concentrated in vacuo to dryness to obtain 1,060 mg of (22S,23S, 24S)-3α,5-cyclo-22,23-diacetoxy-24-ethyl-5-cholestan-6-one (I-f), which upon recrystallization from methanol gives prisms of m.p. 125°–126° C.

I-f NMR (200 MHz) δ: 2.08 (3H, s), 2.11 (3H, s), 2.46 (1H, m), 5.08 (1H, t), 5.29 (1H, q).

EI/MS m/e: 528, 408, 383, 372, 329, 299, 271.

To 530 mg of the crude compound (I-f) are added 5 ml of DMF, 19 mg of p-toluenesulfonic acid and 53 mg of lithium bromide, and the mixture is stirred at 155°–157° C. for 2 hours. Working up as in Example 10 followed by purification on a column gives 419 mg of (22S,23S,24S)-22,23-diacetoxy-24-ethyl-5α-cholest-2-en-6-one (XV-f), which upon recrystallization gives pure crystals of m.p. 116°–118° C.

EXAMPLE 13

Brassinone (XXVIII)

600 mg of 3α,5-cyclo-22R,23R-dihydroxy-6β-benzyloxy-5α-cholest-24-ene (XI B) is dissolved in 6 ml of pyridine, and the solution is cooled to 5° C. 1 ml of acetic anhydride and 10 mg of N,N-dimethylaminopyridine are added, and the mixture is stirred at 5°–15° C. for 18 hours. Water and AcOEt are added to the reaction mixture and the phases are separated. The AcOEt layer is washed successively with water, 1N HCl, water and an aqueous sodium bicarbonate solution, dried over MgSO₄ and concentrated in vacuo to give compound (XVIII). This product is dissolved in 30 ml of AcOEt, and 600 mg of a 5% Pd-C catalyst (50% wet product) is added to effect catalytic reduction at room temperature under an atmosphere of hydrogen. After the adsorption of hydrogen has ceased, the catalyst is filtered off and the filtrate is concentrated to dryness. The residue is purified by chromatography on a column of 30 g of silica gel with AcOEt/benzene (=1/5) to obtain 480 mg of 3α,5-cyclo-22R,23R-diacetoxy-5α-cholestan-6β-ol (II-g). The product is dissolved in 20 ml of AcOEt and subjected to Jones' oxidation at 5° C. to afford 460 mg of crude compound (I-g), which upon recrystallization from methanol gives the compound (I-g) as needles of m.p. 176°–178° C.

400 mg of the crude compound (I-g) is dissolved in 4 ml of DMF, and 20 mg of p-toluenesulfonic acid and 50 mg of lithium bromide are added. The mixture is heated under reflux at 155°–157° C. for 2 hours. AcOEt and water are added to the reaction mixture, and the AcOEt layer is separated, washed with water and an aqueous sodium bicarbonate, dried over MgSO₄ and concentrated in vacuo to dryness to obtain 370 mg of 22R,23R-diacetoxy-5α-cholest-2-en-6-one (XV-g). The product is then subjected, as in Example 9, to osmium oxidation, acetonidation and purification by column chromatography to give 215 mg of (2R,3S,22R,23R)-2,3-isopropyridenedioxy-22,23-diacetoxy-5α-cholestan-6-one (XXIV-g), m.p. 184°–187° C.

5 ml of methanol and 1 ml of a 2N aqueous caustic soda solution are added to 100 mg of the compound (XXIV-g), and the mixture is heated under reflux for 2 hours. After the reaction mixture is cooled, 1.2 ml of 2N HCl and 5 ml of water are added. The mixture is stirred at room temperature for 1 hour and crystals are collected by filtration to obtain 70 mg of brassinone (XXVIII), which upon recrystallization from AcOEt/methanol gives pure crystals of m.p. 258°–260° C.

It is understood that the preceeding representative examples may be varied within the scope of the present specification, both as to the reactants and conditions, by one skilled in the art to achieve essentially the same results.

As many apparently widely different embodiments of the present invention may be made without departing from the spirit and scope thereof, it is to be construed that the present invention is not limited to the specific embodiments thereof as defined in the appended claims.

What is claimed is:

1. A 3α,5-cyclo-22,23-dihydroxy-5α-steroid compound of the formula:

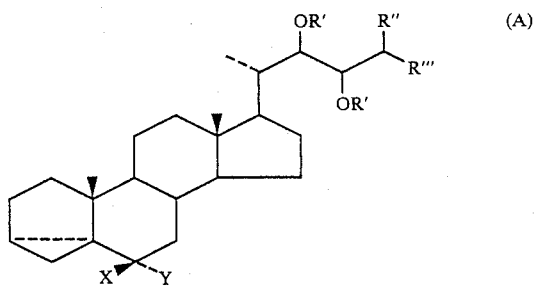

wherein X is a hydroxyl group and Y is a hydrogen atom or X and Y, taken together, form an oxo group; each of the two R, radicals is independently a hydrogen atom, an acyl group derived from a residue of $C_1$–$C_4$ alkanoic acid, a silyl group, a $C_1$–$C_5$ alkoxycarbonyl group or a benzyl group, or the two R, radicals, taken together, form an alkylidene group or a carbonyl group, the stereo-configuration at the 22- and 23-positions being either 22R and 23R, or 22S and 23S; and R″ and R‴ are independently a hydrogen atom or a lower alkyl group with the proviso that when X and Y are taken together to form an oxo group, R″ is a hydrogen atom or a methyl group in the S-configuration and R‴ is isopropyl.

2. A 3α,5-cyclo-22,23-dihydroxy-5α-steroid compound as claimed in claim 1, which is of the general formula:

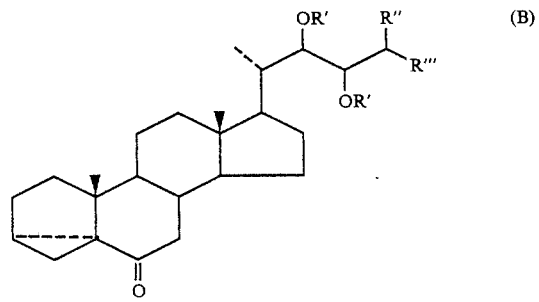

wherein each R′ is a hydrogen atom, an acyl group derived from a residue of a $C_1$–$C_4$ alkanoic acid, a silyl group, an alkoxycarbonyl group or a benzyl group, or the two R′ radicals, taken together, form an alkylidene group or a carbonyl group, the stereo-configuration at the 22- and 23-positions being either 22R and 23R or 22S and 23S; and R″ and R‴ are independently of each other a hydrogen atom or a lower alkyl group wherein R″ is a hydrogen atom or a methyl group in the S-configuration and R‴ is isopropyl.

3. A 3α,5-cyclo-22,23-dihydroxy-5α-steroid compound as claimed in claim 1, which is of the formula:

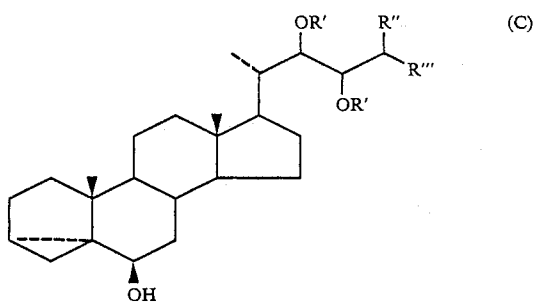

wherein each R' is a hydrogen atom, an acyl group, a silyl group, an alkoxylcarbonyl group or a benzyl group, or the two R' radicals, taken together, form an alkylidene group or a carbonyl group, the stereo-configuration at the 22- and 23-positions being either 22R and 23R or 22S and 23S; and R″ and R‴ are independently of each other a hydrogen atom or a lower alkyl group.

4. A 3α,5-cyclo-22,23-dihydroxy-5α-steroid compound as claimed in claim 1, wherein said R' is a hydrogen atom.

5. A 3α,5-cyclo-22,23-dihydroxy-5α-steroid compound as claimed in claim 1, wherein said R' is an acyl group.

6. A 3α,5-cyclo-22,23-dihydroxy-5α-steroid compound as claimed in claim 1, wherein the two R' radicals, taken together, form an alkylidene group.

7. A 3α,5-cyclo-22,23-dihydroxy-5α-steroid compound as claimed in claim 2, which is (22R,23R,24S)-3α,5-cyclo-22,23-diacetoxy-24-methyl-5α-cholestan-6-one.

8. A 3α,5-cyclo-22,23-dihydroxy-5α-steroid compound as claimed in claim 2, which is (22R,23R,24S)-3α,5-cyclo-22,23-isopropylidenedioxy-24-methyl-5α-cholestan-6-one.

9. A 3α,5-cyclo-22,23-dihydroxy-5α-steroid compound as claimed in claim 3, which is (22R,23R,24S)-3α,5-cyclo-22,23-dihydroxy-24-methyl-5α-cholestan-6β-ol.

10. A 3α,5-cyclo-22,23-dihydroxy-5α-steroid compound as claimed in claim 3, which is (22R,23R,24S)-3α,5-cyclo-22,23-diacetoxy-24-methyl-5α-cholestan-6β-ol.

11. A 3α,5-cyclo-22,23-dihydroxy-5α-steroid compound as claimed in claim 3, which is (22R,23R,24S)-3α,5-cyclo-22,23-isopropylidenedoixy-24-methyl-5α-cholestan-6β-ol.

12. The 3α,5-cyclo-22,23-dihydroxy-5α-steroid compound as claimed in claim 1, wherein said alkylidene group is selected from the group consisting of isopropylidene, n-butylidene-2 and pentylidene-3.

* * * * *